United States Patent
Jordan et al.

(10) Patent No.: US 8,481,547 B2
(45) Date of Patent: Jul. 9, 2013

(54) SUBSTITUTED BENZOTHIAZOLE AND BENZOXAZOLE DERIVATIVES USEFUL AS INHIBITORS OF DPP-1

(75) Inventors: Alfonzo D. Jordan, North Wales, PA (US); Renee L. DesJarlais, Saint Davids, PA (US); Dennis J. Hlasta, Doylestown, PA (US); Michael H. Parker, Chalfont, PA (US); Carsten Schubert, Phoenixville, PA (US); Kimberly White, North Wales, PA (US)

(73) Assignee: Janssen Pharmaceutica NV, Beerse (BE)

( * ) Notice: Subject to any disclaimer, the term of this patent is extended or adjusted under 35 U.S.C. 154(b) by 245 days.

(21) Appl. No.: 12/969,748

(22) Filed: Dec. 16, 2010

(65) Prior Publication Data

US 2011/0152287 A1    Jun. 23, 2011

Related U.S. Application Data

(60) Provisional application No. 61/287,878, filed on Dec. 18, 2009.

(51) Int. Cl.
| | |
|---|---|
| A61K 31/496 | (2006.01) |
| A61K 31/423 | (2006.01) |
| A61K 31/428 | (2006.01) |
| C07D 277/82 | (2006.01) |
| C07D 263/58 | (2006.01) |

(52) U.S. Cl.
USPC ...... 514/254.02; 514/367; 514/375; 544/368; 548/161; 548/222

(58) Field of Classification Search
None
See application file for complete search history.

(56) References Cited

U.S. PATENT DOCUMENTS

2004/0192698 A1    9/2004   Benbow et al.

FOREIGN PATENT DOCUMENTS

| WO | WO 2004/106289 | 12/2004 |
| WO | WO 2006/094003 | 9/2006 |
| WO | WO 2007/025897 A2 | 3/2007 |
| WO | WO 2009/074829 | 6/2009 |
| WO | WO 2009/129371 | 10/2009 |

OTHER PUBLICATIONS

Lutgens et al. The FASEB Journal, vol. 21, pp. 3029-3041 (2007).*
Laine et al. Expert Opin.Ther.Patents 20(4),pp. 497-506 (2010).*
International Search Report, PCT/US2010/060981, dated Feb. 17, 2011.
Methot, N., et al., "In Vivo Inhibition of Serine Protease Processing Requires a High Fractional Inhibition of Cathepsin C", *Molecular Pharmacology*, 2008, pp. 1847-1865, vol. 73(6).
Al-Soud, Y.A., et al., "Synthesis and in vitro antiproliferative activity of new benzothiazole derivative", *ARKIVOC*, 2008, pp. 225-238, vol. XV.
Al-Soud, Y.A., et al., "Synthesis, haracterization and anti-HIV and Antitumor Activities of New Coumarin Derivatives", *Verlag der Zeitchrift fur Naturforschumg*, 2008, pp. 83-89 vol. 63, Issue 1.

* cited by examiner

*Primary Examiner* — Emily Bernhardt
(74) *Attorney, Agent, or Firm* — Mary A. Appollina

(57) ABSTRACT

The present invention is directed to substituted benzothiazole and benzoxazole derivatives, pharmaceutical compositions containing them and their use in the treatment of disorders and conditions modulated by DPP-1.

10 Claims, No Drawings

SUBSTITUTED BENZOTHIAZOLE AND BENZOXAZOLE DERIVATIVES USEFUL AS INHIBITORS OF DPP-1

CROSS-REFERENCE TO RELATED APPLICATIONS

This application claims priority from U.S. Provisional Application Ser. Nos. 61/287,878 filed Dec. 18, 2009, the contents of each of which are hereby incorporated by reference in their entirety.

FIELD OF THE INVENTION

The present invention is directed to novel substituted benzothiazole and benzoxazole derivatives, pharmaceutical compositions containing them and their use in the treatment of disorders and conditions modulated by DPP-1.

BACKGROUND OF THE INVENTION

Chronic Obstructive Pulmonary Disease (COPD) is characterized by the progressive development of irreversible airflow limitation. COPD consists of chronic obstructive bronchitis, with obstruction of small airways, and emphysema, with enlargement of air spaces and destruction of lung parenchyma, loss of lung elasticity, and closure of small airways. In COPD patients, there were increased numbers of neutrophils, cytotoxic T lymphocytes and macrophages in bronchoalveolar lavage (BAL) airways and lung parenchyma. The presence of these inflammatory cells is correlated well with severity of airway obstruction and alveolar wall destruction. It has been shown that neutrophil elastase; cathepsin G and proteinase 3 can produce emphysema and mucus hypersecretion in lab animals. Granzymes A & B are the neutral serine proteases that are expressed exclusively in the granules of activated cytotoxic T lymphocytes. In COPD the protease-antiprotease balance appears to be tipped in favor of increased proteolysis due to increase in polymorphonuclear neutrophil (PMN)-derived proteases, cathepsins and matrix metalloproteases (MMPs). Therefore, a drug that inhibits all or most of the relevant proteases mentioned above is expected to be effective in the treatment of COPD.

Dipeptidyl Peptidase-1 (DPP-1, cathepsin C) is a member of the lysosomal papain-type cysteine protease family that also includes cathepsin B, K, H, L, O, and S. DPP-1 (MW 200 kd) is composed of a dimer of disulfide-linked heavy and light chains, both from a single protein precursor. DPP-1 mRNA is highly expressed in tissues such as lung, spleen, kidney and liver; in inflammatory cells such as PMN, cytotoxic T lymphocytes, alveolar macrophages and mast cells. The biological function of DPP-1 is to convert inactive proenzymes into active enzyme by removing a dipeptide from N-terminal. The proenzymes that are activated by DPP-1 are PMN-derived proteases, granzymes A & B, chymase and tryptase. Since these enzymes play an important pathological role in COPD, inhibition of DDP-1 by small molecules would be a rational therapeutic intervention for COPD. Additional therapeutic indications for a DPP-1 inhibitor are asthma, rhinitis, and rheumatoid arthritis.

There remains a need for inhibitors of DPP-1 for the treatment of DPP-1 mediated disorders and conditions, including but not limited to rheumatoid arthritis, asthma, chronic obstructive pulmonary disease, sepsis, irritable bowel disease, cystic fibrosis, and abdominal aortic aneurism.

SUMMARY OF THE INVENTION

The present invention is directed to compounds of formula (I)

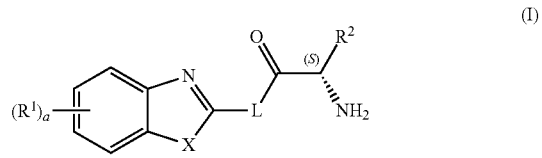

wherein
a is an integer from 0 to 1;
$R^1$ is selected from the group consisting of halogen, $C_{1-4}$alkyl, —$CH_2$—OH, $C_{1-4}$alkoxy, phenyl, 5 to 6 membered heteroaryl, benzo[d][1,3]dioxolyl, —$CO_2H$, —C(O)—$NR^AR^B$, —C(O)—NH—($C_{1-4}$alkyl)-O—($C_{1-4}$alkyl), —C(O)—NH-phenyl, —C(O)—NH—$CH_2$-phenyl, —C(O)—NH—$C_{3-6}$cycloalkyl and —$CH_2$—NH—$C_{3-6}$cycloalkyl;
wherein $R^A$ and $R^B$ are each independently selected from the group consisting of hydrogen and $C_{1-4}$alkyl;
and wherein the phenyl, whether alone or as part of a substituent group is optionally substituted with one or more substituent independently selected from halogen, hydroxy, $C_{1-4}$alkyl, fluorinated $C_{1-4}$alkyl, $C_{1-4}$alkoxy and fluorinated $C_{1-4}$alkoxy;
X is selected from the group consisting of O and S;
L is selected from the group consisting of —NH—$CH_2CH_2$—N($R^C$)— and

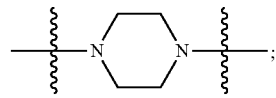

wherein $R^C$ is selected from the group consisting of hydrogen, methyl and ethyl; (and wherein the L substituent group is incorporated into the compound of formula (I) as drawn);
$R^2$ is selected from the group consisting of $C_{1-4}$alkyl, $C_{2-4}$alkenyl, $C_{2-4}$alkynyl, —$CH_2$-thienyl and —$CH_2$-furyl;
and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by DPP-1 (cathepsin C) (selected from the group consisting of rheumatoid arthritis, asthma, chronic obstructive pulmonary disease, sepsis, irritable bowel disease, cystic fibrosis, and abdominal aortic aneurism) in a subject in need thereof comprising administering to the subject a therapeutically effective amount of any of the compounds or pharmaceutical compositions described above.

Another example of the invention is the use of any of the compounds described herein in the preparation of a medicament for treating: (a) rheumatoid arthritis, (b) asthma, (c) chronic obstructive pulmonary disease, (d) sepsis, (e) irritable bowel disease, (f) cystic fibrosis, or (g) abdominal aortic aneurism, in a subject in need thereof.

In another example, the present invention is directed to a compound as described herein for use in a methods for treating a disorder selected from the group consisting of rheumatoid arthritis, asthma, chronic obstructive pulmonary disease, sepsis, irritable bowel disease, cystic fibrosis, and abdominal aortic aneurism, in a subject in need thereof.

DETAILED DESCRIPTION OF THE INVENTION

The present invention is directed to a process for the preparation of compound of formula (I)

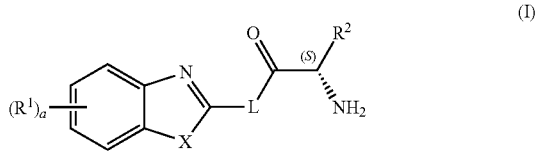

wherein a, $R^1$, X, L and $R^2$ are as defined herein, and pharmaceutically acceptable salts thereof. The compounds of formula (I) of the present invention are inhibitors of DPP-1, useful in the treatment of disorders, diseases and conditions mediated by DPP-1 (cathepsin C), including, but not limited to, rheumatoid arthritis, asthma, chronic obstructive pulmonary disease, sepsis, irritable bowel disease, cystic fibrosis, and abdominal aortic aneurism.

In an embodiment of the present invention a is 0. In another embodiment of the present invention a is 1.

In an embodiment of the present invention, $R^1$ is selected from the group consisting of halogen, $C_{1-2}$alkyl, —$CH_2$—OH, $C_{1-4}$alkoxy, phenyl, 5 to 6 membered heteroaryl, benzo[d][1,3]dioxolyl, —$CO_2H$, —C(O)—$NR^AR^B$, —C(O)—NH—($C_{1-4}$alkyl)-O—($C_{1-4}$alkyl), —C(O)—NH-phenyl, —C(O)—NH—$CH_2$-phenyl, —C(O)—NH—$C_{3-6}$cycloalkyl and —$CH_2$—NH—$C_{3-6}$cycloalkyl; wherein $R^A$ and $R^B$ are each independently selected from the group consisting of hydrogen and $C_{1-4}$alkyl; and wherein the phenyl, whether alone or as part of a substituent group is optionally substituted with one or more substituent independently selected from halogen, hydroxy, $C_{1-4}$alkyl, fluorinated $C_{1-2}$alkyl, $C_{1-4}$alkoxy and fluorinated $C_{1-2}$alkoxy.

In another embodiment of the present invention, $R^1$ is selected from the group consisting of halogen, —$CH_2$—OH, $C_{1-2}$alkoxy, phenyl, 6 membered heteroaryl, benzo[d][1,3]dioxolyl, —$CO_2H$, —C(O)—$NR^AR^B$, —C(O)—NH—($C_{1-4}$alkyl)-O—($C_{1-2}$alkyl), —C(O)—NH-phenyl, —C(O)—NH—$CH_2$-phenyl, —C(O)—NH—$C_{5-6}$cycloalkyl and —$CH_2$—NH—$C_{5-6}$cycloalkyl; wherein $R^A$ and $R^B$ are each independently selected from the group consisting of hydrogen and $C_{1-4}$alkyl; and wherein the phenyl, whether alone or as part of a substituent group is optionally substituted with one to two substituent independently selected from halogen, hydroxy, $C_{1-2}$alkyl, $CF_3$ and $C_{1-2}$alkoxy.

In an embodiment of the present invention, a is 1 and the $R^1$ group is bound at the –6-position of the bicyclic core (i.e. the 6-position of the benzothiazole or benzoxazole core structure).

In another embodiment of the present invention, $R^1$ is selected from the group consisting of 6-(bromo), 6-(carboxy), 6-(hydroxymethyl), 6-(methoxy), 6-(benzo[d][1,3]dioxol-5-yl), 6-(pyrid-3-yl), 6-(4-methylphenyl), 6-(3,4-dimethoxyphenyl), 6-(3,4-difluorophenyl), 6-(4-trifluoromethyl-phenyl), 6-(4-hydroxyphenyl), 6-(2-fluorophenyl), 6-(3,5-dichlorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), 6-(methoxy-n-propyl-amino-carbonyl), 6-(dimethylamino-carbonyl), 6-(4-ethoxyphenyl-amino-carbonyl), 6-(n-propylamino-carbonyl), 6-(cyclohexyl-amino-carbonyl), 6-(3-methoxy-benzyl-amino-carbonyl) and 6-(cyclopentyl-amino-methyl).

In another embodiment of the present invention, $R^1$ is selected from the group consisting of 6-(bromo), 6-(hydroxymethyl), 6-(benzo[d][1,3]dioxol-5-yl), 6-(pyrid-3-yl), 6-(4-methylphenyl), 6-(3,4-dimethoxyphenyl), 6-(3,4-difluorophenyl), 6-(4-trifluoromethyl-phenyl), 6-(4-hydroxyphenyl), 6-(2-fluorophenyl), 6-(3,5-dichlorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), 6-(methoxy-n-propyl-amino-carbonyl), 6-(dimethylamino-carbonyl), 6-(4-ethoxyphenyl-amino-carbonyl), 6-(n-propylamino-carbonyl), 6-(cyclohexyl-amino-carbonyl), 6-(3-methoxy-benzyl-amino-carbonyl) and 6-(cyclopentyl-amino-methyl). In another embodiment of the present invention, $R^1$ is selected from the group consisting of 6-(hydroxymethyl), 6-(benzo[d][1,3]dioxol-5-yl), 6-(pyrid-3-yl), 6-(3,4-dimethoxyphenyl), 6-(3,4-difluorophenyl), 6-(4-hydroxyphenyl), 6-(2-fluorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), and 6-(cyclopentyl-amino-methyl). In another embodiment of the present invention, $R^1$ is selected from the group consisting of 6-(benzo[d][1,3]dioxol-5-yl), 6-(pyrid-3-yl), 6-(4-hydroxyphenyl) and 6-(3,4-dimethoxyphenyl-amino-carbonyl);

In an embodiment of the present invention, X is O. In another embodiment of the present invention, X is S.

In an embodiment of the present invention, L is selected from the group consisting of —NH—$CH_2CH_2$—N($R^C$)— and

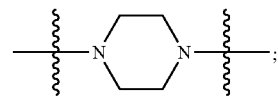

wherein $R^C$ is selected from the group consisting of hydrogen and methyl. In another embodiment of the present invention, L is selected from the group consisting of —NH—$CH_2CH_2$—NH—, —NH—$CH_2CH_2$—N($CH_3$)— and

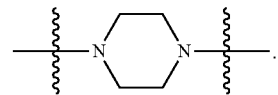

In another embodiment of the present invention L is selected from the group consisting of —NH—$CH_2CH_2$—N($CH_3$)— and

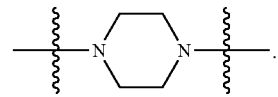

In an embodiment of the present invention, L is

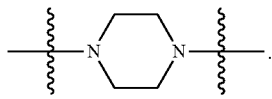 [SMILES: *N1CCN(*)CC1]

In another embodiment of the present invention, L is selected from the group consisting of —NH—CH$_2$CH$_2$—N(R$^C$)— and; wherein R$^C$ is selected from the group consisting of hydrogen, methyl and ethyl. In another embodiment of the present invention, L is selected from the group consisting of —NH—CH$_2$CH$_2$—NH— and —NH—CH$_2$CH$_2$—N(CH$_3$)—. In another embodiment of the present invention, L is —NH—CH$_2$CH$_2$—NH—. In another embodiment of the present invention, L is —NH—CH$_2$CH$_2$—N(CH$_3$)—.

In an embodiment of the present invention, R$^2$ is selected from the group consisting of C$_{1-4}$alkyl, C$_{2-4}$alkynyl, —CH$_2$-thienyl and —CH$_2$-furyl. In another embodiment of the present invention, R$^2$ is selected from the group consisting of C$_{1-2}$alkyl, C$_{2-4}$alkynyl, —CH$_2$-thienyl and —CH$_2$-furyl. In another embodiment of the present invention, R$^2$ is selected from the group consisting of ethyl, n-propyn-2-yl, —CH$_2$-(thien-2-yl), —CH$_2$-(thien-3-yl) and —CH$_2$-(fur-2-yl). In another embodiment of the present invention, R$^2$ is selected from the group consisting of —CH$_2$-(thien-2-yl) and —CH$_2$-(fur-2-yl). In another embodiment of the present invention, R$^2$ is —CH$_2$-(thien-2-yl).

In an embodiment, the present invention is directed to compounds of formula (I) wherein the compound of formula (I) is present in the (S) configuration in an enantiomeric excess of greater than or equal to about 80%, more preferably, in an enantiomeric excess of greater than or equal to about 90%, more preferably still, in an enantiomeric excess of greater than or equal to about 95%, more preferably still, in an enantiomeric excess of greater than or equal to about 98%, most preferably, in an enantiomeric excess of greater than or equal to about 99%.

Additional embodiments of the present invention, include those wherein the substituents selected for one or more of the variables defined herein (i.e. a, R$^1$, X, L, R$^2$) are independently selected to be any individual substituent or any subset of substituents selected from the complete list as defined herein. In another embodiment of the present invention is any single compound or subset of compounds selected from the representative compounds listed in Tables 1 and 2, below.

Representative compounds of the present invention are as listed in Tables 1 to 2, below. One skilled in the art will recognize that in the recitation of the bonding position of the (R$^1$)$_a$ substituent group(s) to the

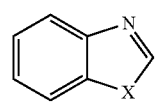

core of the compounds of formula (I) (including in Tables 1 and 2, below), the position of (R$^1$)$_a$ substituent group(s) shall be denoted according to the following numbering scheme:

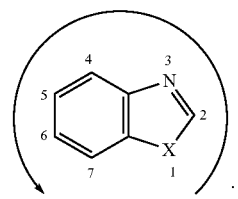

One skilled in the art will further recognize that in Tables 1 and 2 which follow herein, in the column headed "(R$^1$)$_a$", the recitation of #-(substituted group) shall denote the position at which the R$^1$ group is bound to the

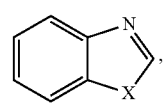

followed by the identification of the substituent group within the parentheses. For example, the notation 6-(3,4-dimethoxy-phenyl-amino-carbonyl) shall denoted a 3,4-dimethoxy-phenyl-amino-carbonyl substituent, bound through the carbonyl portion, and bound at the 6-position of the

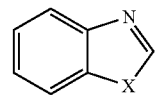

core.

TABLE 1

Representative Compounds of Formula (I)

| ID No | (R$^1$)$_a$ | X | R$^2$ |
|---|---|---|---|
| 1 | a = 0 | S | —CH$_2$-(thien-2-yl) |
| 2 | a = 0 | O | —CH$_2$-(thien-2-yl) |
| 3 | 6-(3,4-dimethoxy-phenyl-amino-carbonyl) | S | —CH$_2$-(thien-2-yl) |
| 4 | 6-(3,4-dimethoxy-phenyl-amino-carbonyl) | S | ethyl |
| 5 | 6-(bromo) | S | —CH$_2$-(thien-2-yl) |
| 6 | 6-(3,4-dimethoxy-phenyl-amino-carbonyl) | S | —CH$_2$-(fur-2-yl) |
| 8 | 6-(4-methyl-phenyl) | S | —CH$_2$-(thien-2-yl) |
| 9 | 6-(benzo[d][1,3]dioxol-5-yl) | S | —CH$_2$-(thien-2-yl) |
| 10 | 6-(3,4-dimethoxy-phenyl) | S | —CH$_2$-(thien-2-yl) |
| 11 | 6-(3,4-difluorophenyl) | S | —CH$_2$-(thien-2-yl) |
| 12 | 6-(3,4-dimethoxy-phenyl-amino-carbonyl) | S | —CH$_2$-(thien-3-yl) |
| 13 | 6-(pyrid-3-yl) | S | —CH$_2$-(thien-2-yl) |
| 14 | 6-(4-trifluoromethyl-phenyl) | S | —CH$_2$-(thien-2-yl) |
| 15 | 6-(4-hydroxyphenyl) | S | —CH$_2$-(thien-2-yl) |
| 16 | 6-(2-fluorophenyl) | S | —CH$_2$-(thien-2-yl) |
| 17 | 6-(3,5-dichlorophenyl) | S | —CH$_2$-(thien-2-yl) |
| 18 | 6-(hydroxymethyl) | S | —CH$_2$-(thien-2-yl) |
| 19 | 6-(cyclopentyl-amino-carbonyl) | S | —CH$_2$-(thien-2-yl) |
| 20 | 6-(4-fluorophenyl-amino-carbonyl) | S | —CH$_2$-(thien-2-yl) |

TABLE 1-continued

Representative Compounds of Formula (I)

| ID No | (R¹)ₐ | X | R² |
|---|---|---|---|
| 21 | 6-(cyclopentyl-amino-methyl) | S | —CH₂-(thien-2-yl) |
| 24 | 6-(n-butyl-amino-carbonyl) | S | —CH₂-(thien-2-yl) |
| 25 | 6-(methoxy-n-propyl-amino-carbonyl) | S | —CH₂-(thien-2-yl) |
| 26 | 6-(carboxy) | S | —CH₂-(thien-2-yl) |
| 27 | 6-(dimethylamino-carbonyl) | S | —CH₂-(thien-2-yl) |
| 28 | 6-(4-ethoxyphenyl-amino-carbonyl) | S | —CH₂-(thien-2-yl) |
| 29 | 6-(n-propyl-amino-carbonyl) | S | —CH₂-(thien-2-yl) |
| 30 | 6-(cyclohexyl-amino-carbonyl) | S | —CH₂-(thien-2-yl) |
| 31 | 6-(3-methoxybenzyl-amino-carbonyl) | S | —CH₂-(thien-2-yl) |

TABLE 2

Representative Compounds of Formula (I)

| ID No | (R¹)ₐ | X | Rᶜ | R² |
|---|---|---|---|---|
| 41 | a = 0 | S | H | ethyl |
| 42 | a = 0 | S | H | n-propyn-2-yl |
| 43 | 6-(methoxy) | S | H | ethyl |
| 44 | a = 0 | O | H | n-propyn-2-yl |
| 45 | a = 0 | O | H | ethyl |
| 46 | a = 0 | S | H | —CH₂-(thien-2-yl) |
| 47 | a = 0 | O | H | —CH₂-(thien-2-yl) |
| 48 | 6-(3,4-dimethoxy-phenyl-amino-carbonyl) | S | methyl | —CH₂-(thien-2-yl) |

In another embodiment, the present invention is directed to compounds of formula (I) whose $IC_{50}$, measured according to the procedure described in Biological Example 1, is less than or equal to about 10 μM, preferably less than or equal to about 5.0 μM, more preferably less than or equal to about 3.0 μM, more preferably less than or equal to about 1.0 μM, more preferably less than or equal to about 0.5 μM.

As used herein, "halogen" shall mean chlorine, bromine, fluorine and iodine.

As used herein, the term "$C_{1-4}$alkyl" whether used alone or as part of a substituent group, shall include any straight and branched carbon chain compositions of one to four carbon atoms. For example, alkyl radicals include methyl, ethyl, propyl, isopropyl, butyl, isobutyl, sec-butyl and t-butyl. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "fluorinated $C_{1-4}$alkyl" shall mean any $C_{1-4}$alkyl group, as herein defined, substituted with at least one fluoro atom. Suitable examples include but are not limited to —CF₃, —CH₂—CF₃, —CF₂—CF₂—CF₂—CF₃, and the like. Preferably, the halogenated or fluorinated alkyl is —CF₃.

As used herein, the term "$C_{2-4}$alkenyl" whether used alone or as part of a substituent group, shall include straight and branched carbon chain compositions of two to four carbon atoms, further containing one or more, preferably one, unsaturated double bond. For example, $C_{2-4}$alkenyl radicals include ethenyl, n-propen-2-yl, n-buten-2-yl, and the like.

As used herein, the term "$C_{2-4}$alkynyl" whether used alone or as part of a substituent group, shall include straight and branched carbon chain compositions of two to four carbon atoms, further containing one or more, preferably one, unsaturated triple bond. For example, $C_{2-4}$alkynyl radicals include ethynyl, n-propyn-2-yl, n-butyn-2-yl, and the like.

As used herein, the term "alkoxy" whether used alone or as part of a substituent group, shall denote an oxygen ether radical of any of the above described straight and branched carbon chain compositions of one to six carbon atoms. For example, alkoxy radicals include methoxy, ethoxy, propoxy, isopropoxy, n-butoxy, isobutoxy, sec-butoxy, t-butoxy, n-pentoxy, and the like. The prefix "$C_{X-Y}$" wherein X and Y are integers, when used with alkoxy shall mean an oxygen radical of any of the above described carbon chain composition of between X and Y carbon atoms. For example, the term "$C_{1-4}$alkoxy" shall mean an oxygen ether radical of any straight or branched carbon chain composition of 1 to 4 carbon atoms. Suitably examples include methoxy, ethoxy, propoxy, isopropoxy, n-butoxy, isobutoxy, sec-butoxy and t-butoxy.

As used herein, unless otherwise noted, the term "fluorinated $C_{1-4}$alkoxy" shall mean any $C_{1-4}$alkoxy group, as herein defined, substituted with at least one fluoro atom. Suitable examples include but are not limited to —OCF₃, —OCH₂—CF₃, —OCF₂—CF₂—CF₂—CF₃, and the like. Preferably, the halogenated or fluorinated alkoxy is —OCF₃.

As used herein, unless otherwise noted, the term "$C_{3-6}$cycloalkyl" shall mean any stable 3-6 membered monocyclic, saturated ring system, for example cyclopropyl, cyclobutyl, cyclopentyl and cyclohexyl.

As used herein, unless otherwise noted, "5 to 6 membered heteroaryl" shall denote any five or six membered, monocyclic aromatic ring structure containing at least one heteroatom selected from the group consisting of O, N and S, optionally containing one to three additional heteroatoms independently selected from the group consisting of O, N and S. The 5 to 6 membered heteroaryl group may be attached at any heteroatom or carbon atom of the ring such that the result is a stable structure. Examples of suitable heteroaryl groups include, but are not limited to, furyl, thienyl, pyrrolyl, oxazolyl, thiazolyl, pyrazolyl, imidazolyl, isoxazolyl, isothiazolyl, triazolyl, thiadiazolyl, tetrazolyl, pyridyl, pyridazinyl, pyrimidinyl, pyrazinyl, pyranyl, and the like. Preferred heteroaryl groups include, but are not limited to, furyl, thienyl, imidazolyl, thiazolyl, pyridyl and pyrimidinyl.

When a particular group is "substituted" (e.g., alkyl, cycloalkyl, phenyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

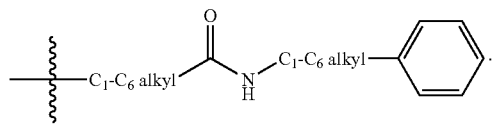

Abbreviations used in the specification, particularly the Schemes and Examples, are as follows
  Boc or BOC=tert-Butoxycarbonyl
  Cbz=Benzyloxy-carbonyl
  DCM=Dichloromethane
  Dess-Martin Reagent=[1,1,1-Triacetoxy-1.1-dihydro-1,2-benziodoxol-3-(1H)-one]
  DIPEA or DIEA=Diisopropylethylamine
  DMF=N,N-Dimethylformamide
  DMSO=Dimethylsulfoxide
  DTT=Dithiothreitol
  EDC or EDCI=1-Ethyl-3-(3-dimethylaminopropyl) carbodiimide
  EtOAc=Ethyl Acetate
  GR-AMC=Glycine-Arginine-amino-4-methyl-coumain
  GSH=Glutathione
  HATU=O-(7-Azabenzotriazol-1-yl)-N,N,N'',N''-Tetramethyl Uronium Hexafluorophosphate
  HBTU=O-(1H-Benzotriazol-1-yl)-N,N,N',N'-tetramethyluronium hexafluorophosphate
  HEPES=4-(2-Hydroxyethyl)-1-Piperizine Ethane Sulfonic Acid
  HOBT or HOBt=1-Hydroxybenzotriazole
  HPLC=High Pressure Liquid Chromatography
  MeOH=Methanol
  MOM=Methoxymethyl
  MTBE=Methyl tert-Butyl Ether
  Na(OAc)$_3$BH=Sodium triacetoxyborohydride
  NMP=N-methyl-2-pyrrolidinone
  Pd$_2$(OAc)$_2$=Palladium(II)acetate
  Pd(dppf)Cl$_2$=Dichloro[1,1'-bis(diphenylphosphine) ferrocene]palladium(II)
  Pd(PPh$_3$)$_4$=Tetrakistriphenylphosphine palladium (0)
  PyBOP=Benzo-triazol-1-yloxytris(pyrrolidino)-phosphonium hexafluorophosphate
  TEA=Triethylamine
  TFA=Trifluoroacetic Acid
  THF=Tetrahydrofuran
  THP=Tetrahydropyranyl
  TMS=Trimethylsilyl As used herein, unless otherwise noted, the term "isolated form" shall mean that the compound is present in a form which is separate from any solid mixture with another compound(s), solvent system or biological environment. In an embodiment, the compound of formula (I) is prepared as an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the compound of formula (I) is present as a substantially pure compound.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "DPP-1 mediated disorder" shall include any condition, disease or disorder which may be mediated through inhibition of DPP-1 activity. One skilled in the art will recognize that disorders mediated by DPP-1 include, but are not limited to (a) disorders of the respiratory tract: including obstructive diseases of the airways including asthma, including bronchial, allergic, intrinsic, extrinsic, exercise-induced, drug induce (including aspirin and NSAID-induced) and dust induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sacroidosis; farmer's lung and related diseases; hypersensitive pnemonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vascullitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

(b) skin disorders: psoriasis, atopic dermatitis, contact dermatatis or other eczematous deramtoses, and delayed-type hypersensitivity reactions; phyto- and photodermatitis; seborrhoeic dermatistis, dermatitis herptiformis, lichen planus, lichen slerosus et atrophica, pyoderma gangrenosum, skin sarcoid, discoid lupus erythematosus, pemphigus, pemphigoid, epidermolysis bullosa, urticaria, angioderma, vasculitides, toxid erythmas, cutaceous eosinopiliass, alopecia areata, male-pattern baldness, Sweet's syndrome, Weber-Christian syndrome, erythema multiforma; cellulitis, both infective and non-infective; panniculitis; cutaceous lymphomas, non-melanoma skin cancer and other dysplastic lesions; drug-induced disorders including fixed-drug eruptions;

(c) eye disorders: blepharitis, conjunctivitis, including perennial and vernal allergic conjunctivitis; iritis; anterior and posterior uveitis; choroiditis; autoimmune, degenerative or inflammatory disorders affecting the retina; opthalmitis including sympathetic opthalmitis; sarcoidosis; infections including viral, fugal and bacterial;

(d) genitourinary disorders: nephritis including interstitial and glomerulnephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction;

(e) allograft rejection disorders: acute and chronic following, for example, transplantation of kidney, heart, liver, lung, bone marrow, skin or cornea or following blood transfusion; or chronic graft versus host disease;

(f) auto-immune and allergic disorders including rheumatoid arthritis, irritable bowel syndrome, systemic lupus erythematosus, multiple sclerosis, Hashimoto's thyroiditis, Grave's disease, Addison's disease, diabetes mellitus, idiopathic thrombocytopaenic purpura, eosinophilic fasciitis, hyper-IgE syndrome, antiphospholipid syndrome and Sazary syndrome;

(g) cancers: including treatment of common cancers including prostate, breast, lung, ovarian, pancreatic, bowel and colon, stomach, skin and brain tumors and malignancies affecting the bone marrow (including leukaemias) and lymphoproliferative systems, such as Hodgkin's and non-Hodgkin's lymphoma; including the prevention and treatment of metastatic disease and tumor recurrences, and paraneoplstic syndrome; and (h) infectious diseases: viral diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoser virus (VZV), rhinovirus, adenovirus, coronavirus, influenza, parainfluenza; bacterial diseases such as tubercuavium, leprosy; other infectious diseases such as fungal diseases, *Chlamydia, candida, aspergillus*, cryptococcal meningitis, *pneumocystis carnii*, cryptosporidiosis, histoplasmosis, toxoplasmosis, trypanosome infection and leishmaniasis.

In another embodiment, the present invention is directed to methods for the treatment and/or prevention of a DDP-1 mediated disorder; wherein the DPP-1 mediated disorder is selected from the group consisting of chronic obstructive pulmonary disease (COPD), asthma, acute lung injury, adult respiratory distress syndrome, abdominal or thoracic aneurism, rheumatoid arthritis, osteoarthritis, multiple sclerosis, sepsis and taxoplasmosis.

In another embodiment, the present invention is directed to methods for the treatment and/or prevention of a DDP-1 mediated disorder; wherein the DPP-1 mediated disorder is selected from the group consisting of rheumatoid arthritis, asthma, chronic obstructive pulmonary disease (COPD), sepsis, irritable bowel disease, cystic fibrosis, and abdominal aortic aneurism.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, 1,2-dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-\max]) \times 100.$$

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Compounds of formula (I) wherein X is S and L is —NH—CH$_2$CH$_2$—NR$^C$— may be prepared according to the process outlined in Scheme 1, below.

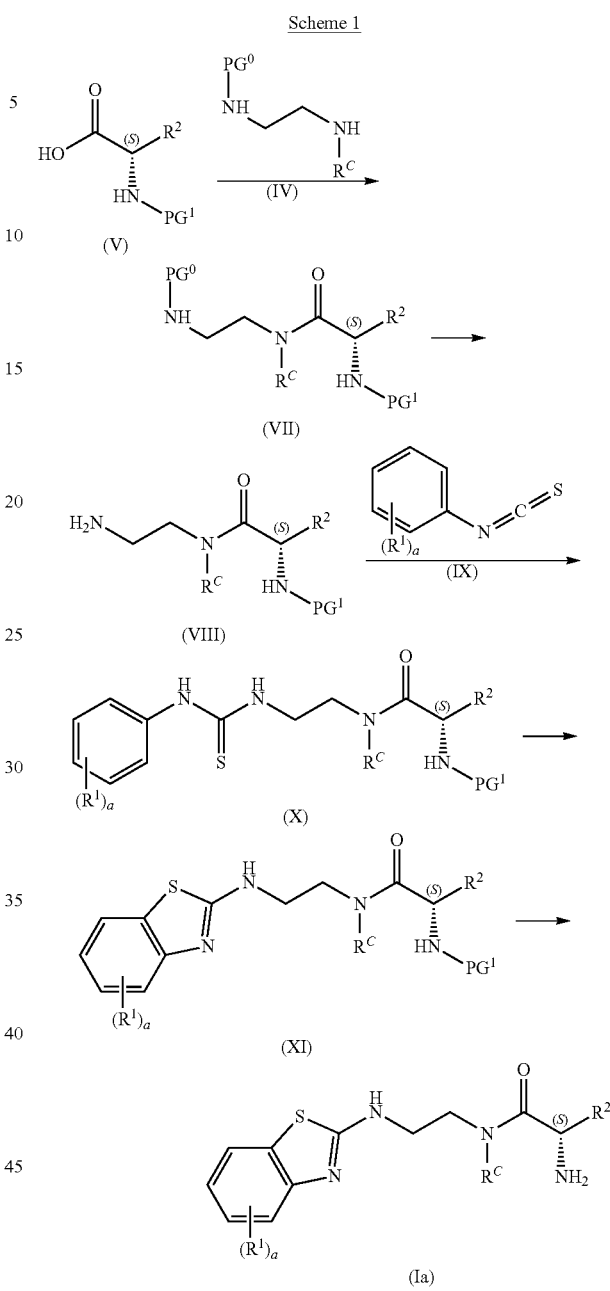

Accordingly, a suitably substituted compound of formula (V), wherein PG$^1$ is a suitably selected nitrogen protecting group such as —C(O)CF$_3$, Boc, CBz, and the like, a known compound or compound prepared by known methods, is reacted with a suitably substituted compound of formula (IV), wherein PG$^0$ is a suitably selected nitrogen protecting group such as Boc, CBz, and the like, a known compound or compound prepared by known methods; in the presence of a suitably selected coupling system such as HOBt in combination with EDC, and the like; in the presence of a suitably selected organic base such as TEA, DIPEA, pyridine, and the like; in a suitably selected organic solvent such as DCM, DMF, and the like; to yield the corresponding compound of formula (VII).

The compound of formula (VII) is selectively de-protected according to known methods; to yield the corresponding compound of formula (VIII). For example, wherein $PG^O$ is CBz, the compound of formula (VII) is de-protected by reacting with 1,4-cyclohexadiene or 10% palladium on carbon, in a solvent such as ethanol.

The compound of formula (VIII) is reacted with a suitably substituted compound of formula (IX), a known compound or compound prepared by known methods; in a suitably selected organic solvent such as DCM, THF, chloroform, and the like, to yield the corresponding compound of formula (X).

The compound of formula (X) is reacted with benzyl-trimethyl-ammonium tribromide, a known compound; in a suitably selected organic solvent such as DCM, 1,2-dimethoxyethane, acetonitrile, and the like, to yield the corresponding compound of formula (XI).

The compound of formula (XI) is de-protected according to known methods; to yield the corresponding compound of formula (Ia). For example, wherein $PG^1$ is —C(O)CF$_3$, the compound of formula (XI) is de-protected by reacting with a suitably selected base such as NaOH, LiOH, and the like, in a suitably selected solvent such as THF, water, and the like.

Compounds of formula (I) wherein L is —NH—CH$_2$CH$_2$—N(R$^C$)— may alternatively be prepared according to the process outlined in Scheme 2, below.

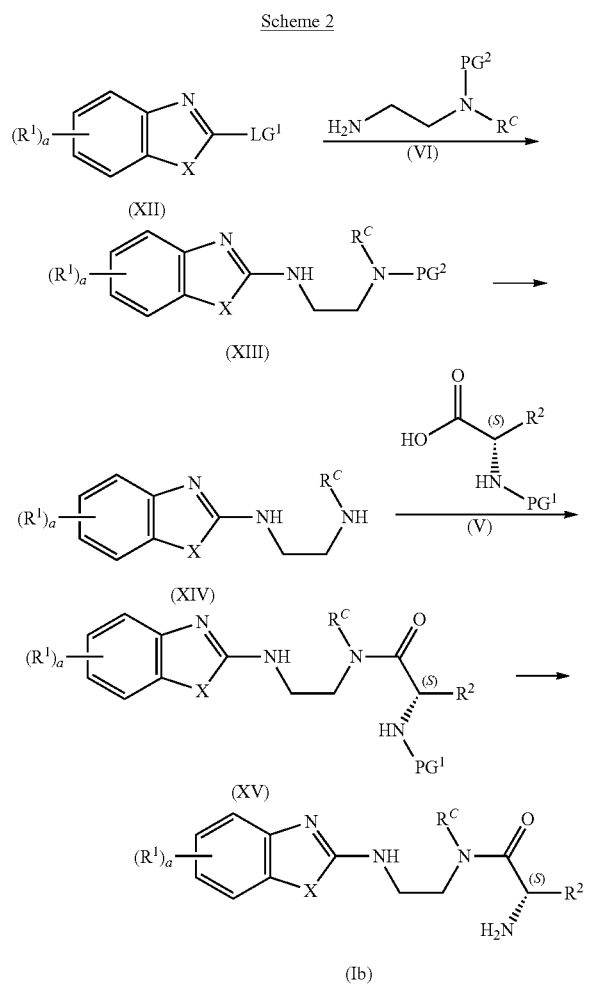

Accordingly, a suitably substituted compound of formula (XII), wherein $LG^1$ is a suitably selected leaving group such as bromo, chloro, and the like, a known compound or compound prepared by known methods, is reacted with a suitably substituted compound of formula (VI), wherein $PG^2$ s a suitably selected nitrogen protecting group such as Boc, CBz, and the like, a known compound or compound prepared by known methods; in the presence of an organic base such as DIPEA, TEA, pyridine, and the like; in a suitably selected organic solvent such as NMP, DMF, and the like; preferably at an elevated temperature in the range of from about 80° C. to about 125° C., for example, at about 120° C.; to yield the corresponding compound of formula (XIII).

The compound of formula (XIII) is de-protected according to known methods, to yield the corresponding compound of formula (XIV). For example, wherein $PG^2$ is Boc, the compound of formula (XIII) is de-protected by reacting with a suitably selected acid such as HCl, TFA, and the like, in a suitably selected organic solvent such as 1,4-dioxane, DCM, and the like.

The compound of formula (XIV) is reacted with a suitably substituted compound of formula (V), wherein $PG^1$ is a suitably selected nitrogen protecting group such as Boc, CBz, and the like, a known compound or compound prepared by known methods; in the presence of a suitably selected coupling system such as HOBt in combination with EDCI, and the like; in the presence of a suitably selected organic base such as TEA, DIPEA, pyridine, and the like; in a suitably selected organic solvent such as DCM, DMF, and the like; to yield the corresponding compound of formula (XV).

The compound of formula (XV) is de-protected according to known methods to yield the corresponding compound of formula (Ib). For example, wherein $PG^3$ is Boc, the compound of formula (XV) is de-protected by reacting with a suitably selected acid such as HCl, TFA, and the like, in a suitably selected organic solvent such as 1,4-dioxane, DCM, and the like.

One skilled in the art will recognize that compounds of formula (XII) wherein a is 1 and wherein $R^1$ is selected from the group consisting of —C(O)—NR$^A$R$^B$, —C(O)—NH—(C$_{1-4}$alkyl)-O—(C$_{1-4}$alkyl), —C(O)—NH-phenyl, —C(O)—NH—CH$_2$-phenyl and —C(O)—NH—C$_{3-6}$cycloalkyl may be prepared as described in Scheme 3, below.

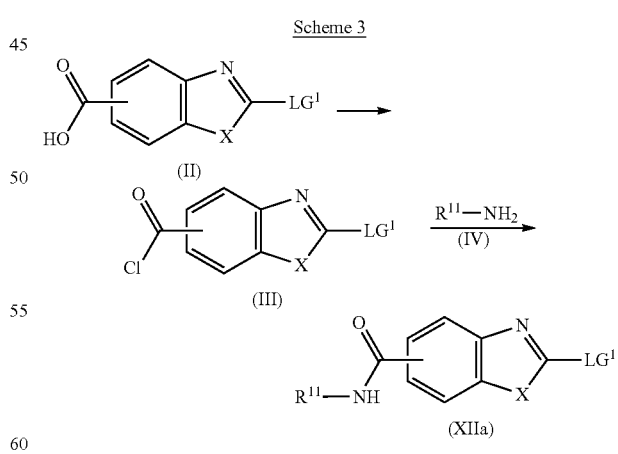

Accordingly, a suitably substituted compound of formula (II), wherein $LG^1$ is a suitably selected leaving group such as bromo, chloro, and the like, a known compound or compound prepared by known methods, is reacted with a suitably selected source of chlorine such as oxalyl chloride, thionyl chloride, and the like; in the presence of a catalytic amount of DMF; in a suitably selected solvent such as DCM, THF, and the like; to yield the corresponding compound of formula (III).

The compound of formula (III) is reacted with a suitably substituted amine, a compound of formula (IV), wherein $R^{11}$ is $-NR^AR^B$, $-NH-(C_{1-4}alkyl)-O-(C_{1-4}alkyl)$, $-NH-$phenyl, $-NH-CH_2$-phenyl and $-NH-C_{3-6}$cycloalkyl, a known compound or compound prepared by known methods; in the presence of an organic base such as DIPEA, TEA, pyridine, and the like; in an aprotic organic solvent such as DCM, THF, chloroform, and the like; to yield the corresponding compound of formula (XIIIa).

Compounds of formula (I) wherein L is

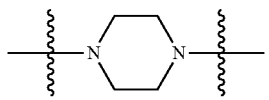

may be prepared according to the process outlined in Scheme 4, below.

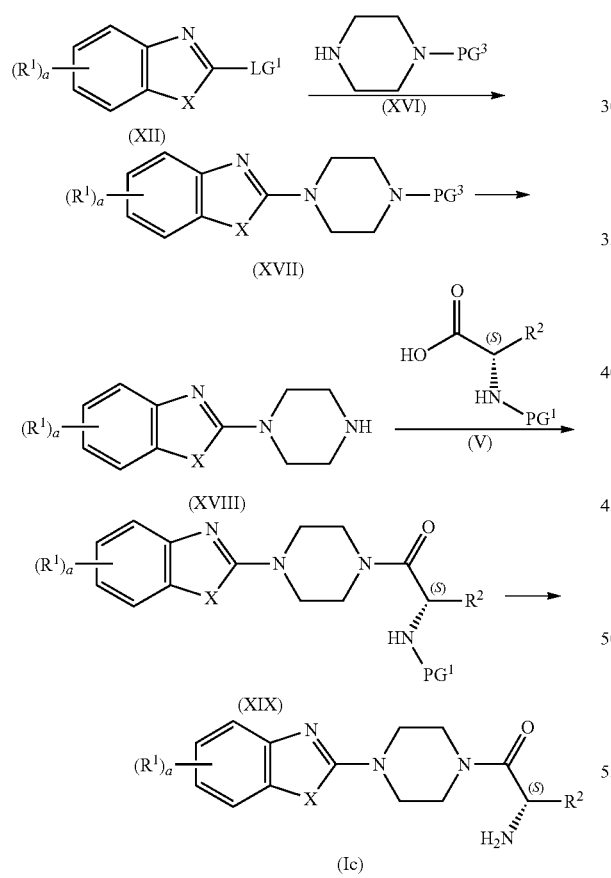

Accordingly, a suitably substituted compound of formula (XII), wherein $LG^1$ is a suitably selected leaving group such as bromo, chloro, and the like, a known compound or compound prepared by known methods, is reacted with a suitably substituted compound of formula (XVI), wherein $PG^3$ is a suitably selected nitrogen protecting group such as BOC, CBz, and the like, a known compound or compound prepared by known methods; in the presence of a suitably selected organic base such as DIPEA, TEA, pyridine, and the like; in a suitably selected organic solvent such as NMP, DMF, and the like; preferably at an elevated temperature in the range of from about 80° C. to about 125° C., for example, at about 120° C.; to yield the corresponding compound of formula (XVII).

The compound of formula (XVII) is de-protected according to known methods, to yield the corresponding compound of formula (XVIII). For example, wherein $PG^3$ is Boc, the compound of formula (XVII) is de-protected by reacting with a suitably selected acid such as HCl, TFA, and the like, in a suitably selected organic solvent such as 1,4-dioxane, DCM, and the like.

The compound of formula (XVIII) is reacted with a suitably substituted compound of formula (V), wherein $PG^1$ is a suitably selected nitrogen protecting group such as $-C(O)CF_3$, Boc, CBz, and the like, a known compound or compound prepared by known methods, in the presence of a suitably selected coupling system such as HOBt in combination with EDCI, and the like; in the presence of a suitably selected organic base such as TEA, DIPEA, pyridine, and the like; in a suitably selected organic solvent such as DCM, DMF, and the like; to yield the corresponding compound of formula (XIX).

The compound of formula (XIX) is de-protected according to known methods to yield the corresponding compound of formula (Ic). For example, wherein $PG^1$ is Boc, the compound of formula (XIX) is de-protected by reacting with a suitably selected acid such as HCl, TFA, and the like, in a suitably selected organic solvent such as 1,4-dioxane, DCM, and the like.

One skilled in the art will recognize that compounds of formula (Ic) wherein $R^1$ is selected from the group consisting of $C_{1-4}$alkyl, optionally substituted phenyl, 5 to 6 membered heteroaryl and benzo[d][1,3]dioxolyl, may alternatively be prepared by reacting as described in Scheme 5, below.

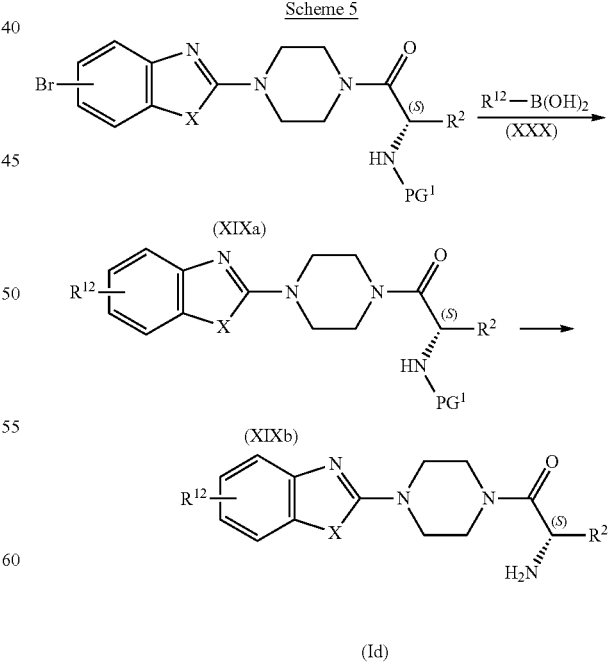

Accordingly, a suitably substituted compound of formula (XIXa), a compound of formula (XIX) wherein a is 1 and $R^1$ is bromo, prepared for example as described in Scheme 4 above, is reacted with a suitably substituted boronic acid compound of formula (XXX), wherein $R^{12}$ is selected from the group consisting of $C_{1-4}$alkyl, optionally substituted phenyl, 5 to 6 membered heteroaryl and benzo[d][1,3]dioxolyl, a known compound or compound prepared by known methods; in the presence of a suitably selected coupling agent such as $Pd(PPh_3)_4$, $Pd(OAc)_2$, $Pd(dppf)Cl_2$, and the like; in the presence of a suitably selected inorganic base such as $K_2CO_3$, and the like; in a suitably selected solvent or mixture thereof such as 1,4-dioxane, water, a mixture of THF and water, and the like; to yield the corresponding compound of formula (XIXb).

The compound of formula (XIXb) is de-protected according to known methods, for example, as described in Scheme 4 above, to yield the corresponding compound of formula (Id).

Compounds of formula (I) wherein L is

or —NH—$CH_2CH_2$—$N(R^C)$— and wherein $R^1$ is selected from the group consisting of —C(O)—$NR^A R^B$, —C(O)—NH—($C_{1-4}$alkyl)-O—($C_{1-4}$alkyl), —C(O)—NH-phenyl, —C(O)—NH—$CH_2$-phenyl and —C(O)—NH—$C_{3-6}$cycloalkyl may alternatively be prepared according to the process outlined in Scheme 6, below.

Scheme 6

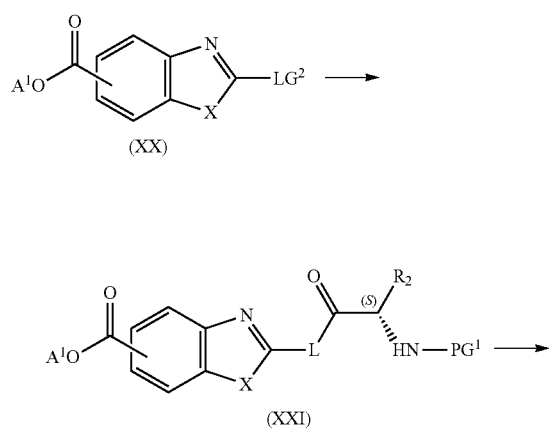

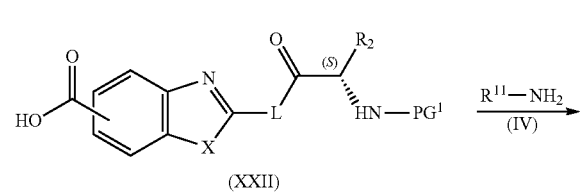

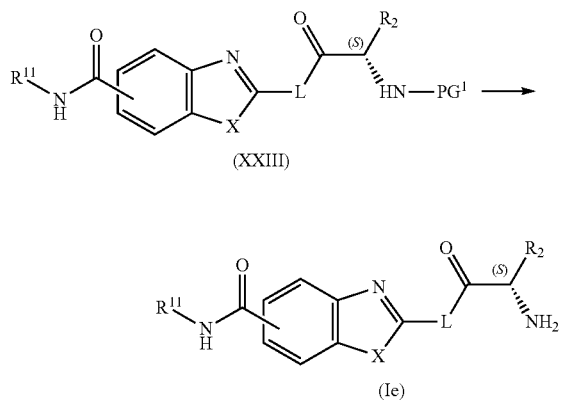

Accordingly, a suitably substituted compound of formula (XX), wherein $A^1$ is $C_{1-4}$alkyl, preferably methyl or ethyl, and wherein $LG^2$ is a suitably selected leaving group such as bromo, chloro, and the like, a known compound or compound prepared by known methods, is reacted as herein described, to yield the corresponding compound of formula (XXI), wherein $PG^1$ is a suitably selected nitrogen protecting group such as Boc, CBz, and the like. For example, the compound of formula (XX) may be reacted with a suitably substituted compound of formula (VI), de-protected and then reacted with a suitably substituted compound of formula (V), according to the process outlined in Scheme 2 above. Alternatively, the compound of formula (XX) may be reacted with a suitably substituted compound of formula (XVI), de-protected and then reacted with a suitably substituted compound of formula (V), according to the process outlined in Scheme 4 above.

The compound of formula (XXI) is reacted with a suitably selected base such as NaOH, LiOH, and the like; in a suitably selected organic solvent such as methanol, ethanol, and the like; to yield the corresponding compound of formula (XXII).

The compound of formula (XXII) is reacted with a suitably substituted compound of formula (IV), wherein $R^{11}$ is —$NR^A R^B$, —NH—($C_{1-4}$alkyl)-O—($C_{1-4}$alkyl), —NH-phenyl, —NH—$CH_2$-phenyl and —NH—$C_{3-6}$cycloalkyl, a known compound or compound prepared by known methods; in the presence of a suitably selected coupling agent such as HBTU, HATU, PyBOP, and the like; in the presence of a suitably selected organic base such as TEA, DIPEA, pyridine, and the like; in a suitably selected organic solvent such as DMF, and the like; to yield the desired, corresponding compound of formula (XXIII).

The compound of formula (XXIII) is de-protected according to known methods, to yield the corresponding compound of formula (Ie). For example, wherein $PG^1$ is Boc, the compound of formula (XIX) is de-protected by reacting with a suitably selected acid such as HCl, TFA, and the like, in a suitably selected organic solvent such as 1,4-dioxane, DCM, and the like.

Compounds of formula (I) wherein L is

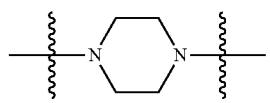

and wherein $R^1$ is —$CH_2$—OH or —$CH_2$—NH—$C_{3-6}$cycloalkyl, may be prepared according the process outlined in Scheme 7, below.

Scheme 7

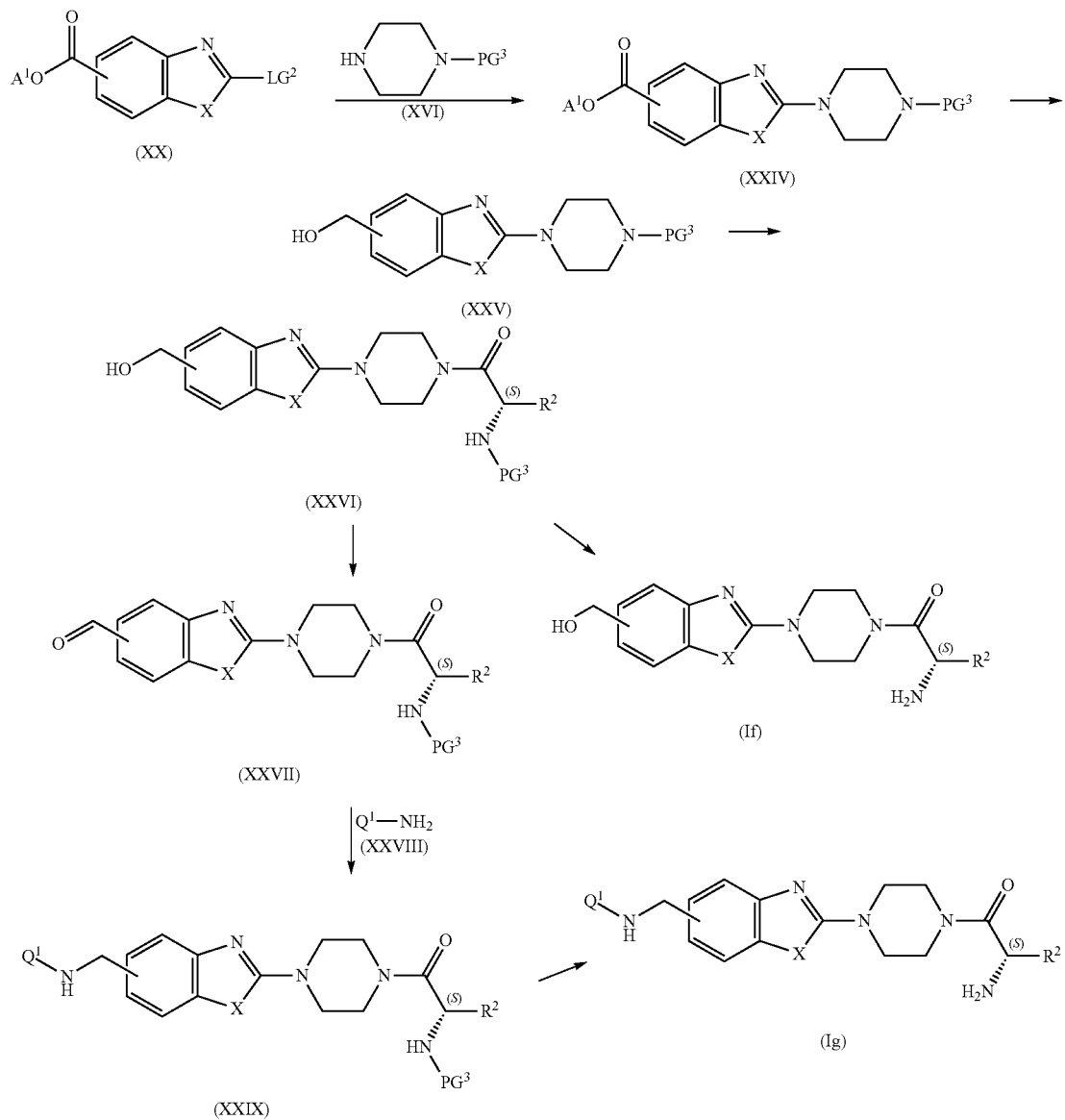

Accordingly, a suitably substituted compound of formula (XX), wherein $A^1$ is $C_{1-4}$alkyl, preferably methyl or ethyl, and wherein $LG^2$ is a suitably selected leaving group such as bromo, chloro, and the like, a known compound or compound prepared by known methods, is reacted with a compound of formula (XVI), wherein $PG^3$ is a suitably selected nitrogen protecting group such as Boc, CBz, and the like, a known compound or compound prepared by known methods; in the presence of a suitably selected inorganic base such as $K_2CO_3$, $Cs_2CO_3$, and the like; in a suitably selected organic solvent such as acetonitrile, DMF, and the like; to yield the corresponding compound of formula (XXIV).

The compound of formula (XXIV) is reacted with a suitably selected reducing agent such LiBH$_4$, LiAlH$_4$, NaBH$_4$, and the like; in a suitably selected organic solvent such as THF, diethyl ether, and the like; to yield the corresponding compound of formula (XXV).

The compound of formula (XXV) is then de-protected according to known methods, reacted with a suitably substituted compound of formula (V), as described in Scheme 4 above, to yield the corresponding compound of formula (XXVI).

The compound of formula (XXVI) is then de-protected according to known methods, to yield the corresponding compound of formula (If), a compound of formula (I) wherein $R^1$ is hydroxymethyl.

Alternatively, the compound of formula (XXVI) is reacted with a suitably selected oxidizing agent such as Dess-Martin reagent, Pyridinium chlorochromate (PCC), a mixture of DMS/oxalyl chloride, and the like; in a suitably selected organic solvent such as DCM, acetonitrile, and the like; to yield the corresponding compound of formula (XXVII).

The compound of formula (XXVII) is reacted with a suitably substituted compound of formula (XXVIII), wherein $Q^1$ is $C_{3-6}$cycloalkyl, a known compound or compound prepared by known methods; in the presence of a suitably selected reducing agent such as Na(OAc)$_3$BH, NaCNBH$_3$, and the like; in a suitably selected organic solvent such as DCM, dichloroethane, methanol, and the like; to yield the corresponding compound of formula (XXIX).

The compound of formula (XXIX) is de-protected according to known methods, to yield the corresponding compound of formula (Ig). For example, wherein $PG^1$ is BOC, the compound of formula (XXIX) is de-protected by reacting with a suitably selected acid such as HCl, TFA, and the like, in a suitably selected organic solvent such as 1,4-dioxane, DCM, and the like.

One skilled in the art will recognize that compounds of formula (I) wherein L is —NH—$CH_2CH_2$—N($R^C$)— may similarly be prepared according to the process outlined in Scheme 7 above, by selecting and substituting a suitably substituted compound of formula (VI) for the compound of formula (XVI).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1,000 mg or any amount or range therein, and may be given at a dosage of from about 0.01 mg/kg/day to about 100 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1,000 mg of the compound, or any amount or range therein; preferably about 1.0 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by DPP-1 is required.

The daily dosage of the products may be varied over a wide range from 0.1 to about 10,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1,000 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.1 mg/kg to about 50.0 mg/kg of body weight per day, or any amount or range therein. More preferably, from about 0.1 mg/kg to about 25.0 mg/kg of body weight per day, or any amount or range therein. More preferably, from about 0.1 mg/kg to about 15.0 mg/kg of body weight per day, or any amount or range therein. More preferably, from about 0.1 mg/kg to about 10.0 mg/kg of body weight per day, or any amount or range therein. More preferably, from about 0.1 mg/kg to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. For example, Methot, N., et al., "In Vivo Inhibition of Serine Protease Processing Requires a High Fractional Inhibition of Cathepsin C", *Molecular Pharmacology*, (2008), Vol. 73, No. 6, pp 1857-1865 disclose an in vivo assay in rats for measuring inhibition of Cathepsin C (DPP-1).

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #41

(S)-2-amino-N-(2-(benzo[d]thiazol-2-ylamino)ethyl)butanamide hydrochloride

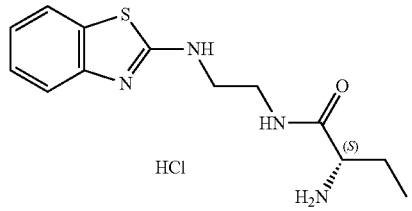

Step A:

To an ice cold mixture of N-2-trifluoroacetamido-L-butanoic acid (1.0079 g, 5.00 mmol) and N-hydroxybenzotriazole (886 mg, 6.60 mmol) in dichloromethane (30 mL) was added N-carbobenzoxy-1,2-diaminoethane hydrochloride (1.5058 g, 6.50 mmol), triethylamine (2.3 mL, 16.5 mmol) and 1-[3-dimethylaminopropyl]-3-ethyl carbodiimide hydrochloride (1.2616 g, 6.60 mmol). The resulting mixture was stirred at 0° C. for 2 hours ("h") and then at room temperature for 18 h. The resulting mixture was diluted with DCM (50 mL), then washed with aqueous sodium chloride (2×25 mL). The organic layer was dried over sodium sulfate, filtered and concentrated. The resulting residue was purified by flash chromatography, eluting with 70% ethyl acetate in heptane to yield (S)-benzyl 2-(2-(2,2,2-trifluoroacetamido)butanamido)ethylcarbamate as a white solid.

$^1$HNMR (DMSO-$d_6$) δ 9.49 (d, J=7.88 Hz, 1H), 8.19-8.17 (m, 1H), 7.39 (m+s, 6H), 5.00 (s, 2H), 4.20-3.99 (m, 1H), 3.31-3.03 (m, 4H), 1.81-1.58 (m, 2H), 0.83 (t, J=7.34, 7.34 Hz, 3H). MS MH$^+$=376.

Step B:

To a heterogenous mixture of (S)-benzyl 2-(2-(2,2,2-trifluoroacetamido)butanamido)ethylcarbamate (1.1913 g, 3.20 mmol) and 10% Pd on carbon (1.2236 g) in ethanol (75 mL) was added 1,4-cyclohexadiene (3.0 mL, 32.0 mmol). The resulting mixture was stirred overnight at room temperature. The resulting mixture was then filtered through a bed of CELITE® and concentrated. The residue was dissolved in chloroform and filtered again through CELITE® to yield (S)—N-(2-aminoethyl)-2-(2,2,2-trifluoroacetamido)butanamide as an unstable oil which was stored in the freezer.

$^1$HNMR (CDCl$_3$) δ 6.91 (m, 1H), 6.77 (m, 1H), 4.20-3.99 (m, 1H), 3.60 (m, 2H), 3.40-2.83 (m, 2H), 2.89-284 (m, 2H), 1.98-1.68 (m, 2H), 0.97-0.92 (m, 3H). MS MH$^+$=242

Step C:

To a solution of the compound prepared in STEP B above (263 mgs, ca 1.0 mmol) in methylene chloride (10 mL) was added phenyl isothiocyanate (120 μL, 1.00 mmol). The resulting mixture was stirred at room temperature for 1 h, then treated with benzyltrimethylammonium tribromide (389.4 mgs 1.00 mmol). The resulting mixture was then stirred overnight. The reaction was quenched with aqueous sodium bicarbonate and the mixture extracted into methylene chloride. The organic layer was dried over sodium sulfate, then filtered and concentrated to yield a residue which was purified by normal phase column chromatography, eluting with 90:10:1 chloroform:methanol:concentrated ammonium hydroxide to yield (S)—N-(2-(benzo[d]thiazol-2-ylamino)ethyl)-2-(2,2,2-trifluoroacetamido)butanamide as a yellow solid.

$^1$HNMR (DMSO-$d_6$) δ 9.49 (d, J=7.88 Hz, 1H), 8.44-8.30 (m, 1H), 8.06-8.03 (m, 1H), 7.66 (d, J=7.66 Hz, 1H), 7.51-7.30 (m, 1H), 7.24-7.19 (m, 1H), 7.04-6.99 (m, 1H), 4.22-4.15 (m, 1H), 3.43-3.21 (m, 4H), 1.81-1.58 (m, 2H), 0.83 (t, J=7.34, 7.34 Hz, 3H).

Step D:

To an ice cold solution of the compound prepared in STEP C above (220.0 mgs, 0.545 mmol) in a 1:4 tetrahydrofuran:methanol mixture was added 3N aqueous sodium hydroxide solution (0.6 mL). The resulting mixture was stirred overnight at room temperature. After 1 day ("d"), additional 3N aqueous sodium hydroxide solution (1 mL) was added and the mixture stirred for 4 h. The resulting mixture was extracted into chloroform. The organic layer was dried over sodium sulfate, filtered and concentrated to yield a residue. The residue was purified by preparative thin layer chromatography, eluting with a 90:10:1 chloroform:methanol:concentrated ammonium hydroxide mixture to yield the title compound, as its corresponding free base. Acidification of the free base in chloroform, with 1 N hydrogen chloride in diethyl ether yielded the corresponding di-hydrochloride salt as a moisture-sensitive solid.

$^1$HNMR (DMSO-$d_6$) δ 10.41-9.73 (br s, 1H), 8.83 (m, 1H), 8.32 br s, 3H), 7.82 (d, J=7.86 Hz, 1H), 7.55 (d, J=8.06 Hz, 1H), 7.38 (t, J=7.40 Hz, 7.40 Hz, 1H), 7.21 (t, J=7.61 Hz, 7.61 Hz, 1H), 3.69-3.43 (m, 5H), 1.78-1.68 (m, 2H), 0.84 (t, J=7.34, 7.34 Hz, 3H).

Example 2

Compound #43

(S)-2-amino-N-(2-(6-methoxybenzo[d]thiazol-2-ylamino)ethyl)butanamide hydrochloride

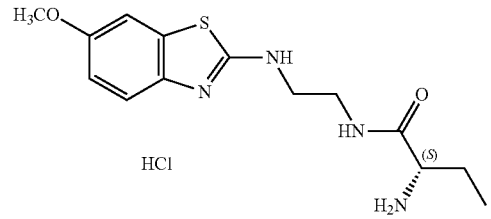

Step A:

To a solution of (S)—N-(2-aminoethyl)-2-(2,2,2-trifluoroacetamido)butanamide (276.6 mg, ca, 1.10 mmol) in dichloromethane (10 mL) was added 4-methoxyphenyl isothiocyanate (120 μL, 0.868 mmol). and the resulting mixture was stirred for 72 h at room temperature. The resulting mixture was then concentrated to an oil, which was purified by column chromatography, eluting with 6% methanol in chloroform to yield (R)—N-(2-(3-(4-methoxyphenyl)thioureido)ethyl)-2-(2,2,2-trifluoroacetamido)butanamide as a solid.

$^1$HNMR (DMSO-$d_6$) δ 9.63-9.42 (m, 2H), 8.24-8.22 (m 1H), 7.50-7.40 (m, 1H), 7.32-7.14 (m, 2H), 6.91-6.85 (m, 2H), 4.18-4.14 (m, 1H), 3.53-3.51 (m, 2H), 3.35-3.22 (m, 2H), 3.73 (s, 3H), 1.81-1.58 (m, 2H), 0.83 (t, J=7.34, 7.34 Hz, 3H). MS MH$^+$=407.

Step B:

A solution of (R)—N-(2-(3-(4-methoxyphenyl)thioureido)ethyl)-2-(2,2,2-trifluoroacetamido)butanamide (412.5 mgs, 1.0 mmol) in methylene chloride (10 mL) was treated with benzyltrimethylammonium tribromide (389.4 mgs 1.00 mmol) and the resulting mixture stirred overnight. The reaction was then quenched with aqueous sodium bicarbonate and extracted into methylene chloride. The organic layer was dried over sodium sulfate, then filtered and concentrated to yield a residue which was purified by normal phase column chromatography, eluting with 5% methanol in chloroform to yield (S)—N-(2-(6-methoxybenzo[d]thiazol-2-ylamino) ethyl)-2-(2,2,2-trifluoroacetamido)-butanamide as a yellow solid.

$^1$HNMR (DMSO-d$_6$) δ 9.49 (d, J=7.88 Hz, 1H), 8.36-8.14 (m, 1H), 7.84-7.81 (m, 1H), 7.37-7.28 (m, 2H), 6.88-6.80 (m, 1H), 4.46-4.12 (m, 1H), 3.73 (s, 3H), 3.55-3.27 (m, 4H), 1.81-1.58 (m, 2H), 0.83 (t, J=7.34, 7.34 Hz, 3H). MS MH+=405.

Step C:

To an ice cold solution of (S)—N-(2-(6-methoxybenzo[d] thiazol-2-ylamino)ethyl)-2-(2,2,2-trifluoroacetamido)-butanamide (229 mg, 0.567 mmol) in a 1:4 tetrahydrofuran: methanol mixture was added 3N aqueous sodium hydroxide solution (1.2 mL). The resulting mixture was stirred overnight at room temperature. After 1 d, additional 3N aqueous sodium hydroxide solution (0.6 mL) was added and the mixture stirred for 4 h. The resulting mixture was extracted into chloroform. The organic layer was dried over sodium sulfate, filtered and concentrated to a residue. The residue was purified by preparative thin layer chromatography, eluting with a 90:10:1 chloroform:methanol:concentrated ammonium hydroxide mixture to yield the title compound as its corresponding free base. Acidification of the free base in chloroform, with 1 N hydrogen chloride in diethyl ether yielded the corresponding di-hydrochloride salt as an off-white solid.

$^1$HNMR (DMSO-d$_6$) δ 9.97-9.65 (br s, 1H), 8.81-8.78 (m, 1H), 8.28 (br s, 3H), 7.48-7.43 (m, 2H), 6.99-6.95 (m, 1H), 3.76 (s, 3H), 3.68-3.42 (m, 5H), 1.77-1.68 (m, 2H), 0.84 (t, J=7.34, 7.34 Hz, 3H). MS MH+=309.

Example 3

Compound #46

(S)-2-amino-N-(2-(benzo[d]thiazol-2-ylamino) ethyl)-3-(thiophen-2-yl)propanamide hydrochloride

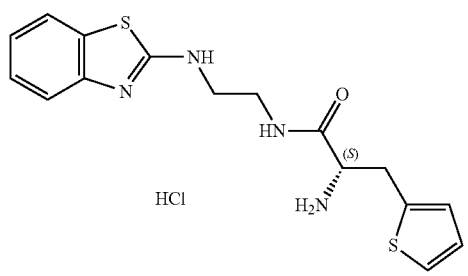

Step A:

2-Bromo-1,3-benzothiazole (505.5 mg, 2.36 mmol) and N-(2-aminoethyl) carbamic acid tert-butyl ester (1.1356 g, 7.10 mmol) were stirred in a preheated oil bath (125° C.) for 5 h. The solid mass was dissolved in chloroform, and the resulting solution was washed with aqueous sodium bicarbonate then dried, filtered and concentrated to a yield a residue. The residue was purified by flash chromatography, eluting with 60% ethyl acetate in hexane to yield tert-butyl 2-(benzo[d]thiazol-2-ylamino)ethylcarbamate as a white amorphous solid.

$^1$HNMR (DMSO-d$_6$) δ 8.05-8.01 (m, 1H), 7.65 (d, J=7.75 Hz, 1H), 7.37 (d, J=7.92 Hz, 1H), 7.23-7.19 (m, 1H), 7.03-6.98 (m, 1H), 6.96-6.92 (m, 1H), 3.41-3.36 (m, 2H), 3.28-3.12 (m, 2H), 1.37 (s, 9H). MS (MH+)=294.

Step B:

tert-Butyl 2-(benzo[d]thiazol-2-ylamino)ethylcarbamate (597.7 mgs, 2.04 mmol) was dissolved in 1,4-dioxane (6 mL) then treated with 4N HCL in 1,4-dioxane (6 mL) and stirred for 3 h. A white separated solid was collected by filtration, washed with diethyl ether and dried in vacuum oven overnight at room temperature to yield the hydrochloride salt of N1-(benzo[d]thiazol-2-yl)ethane-1,2-diamine as an off-white amorphous solid.

$^1$HNMR (DMSO-d$_6$) δ 9.80-9.48 (br s, 1H), 8.27 (s, 4H), 7.83 (d, J=7.85 Hz, 1H), 7.55 (d, J=7.96 Hz, 1H), 7.40-7.35 (m, 1H), 7.23-7.19 (m, 1H), 3.78-3.76 (m, 2H) (m, 2H), 3.17-3.11 (m, 2H); MS (MH+)=194.

Step C:

Boc-(β)-(2-thienyl)-L-alanine (218.5 mg, 0.805 mmol), N-hydroxybenzotriazole hydrate (109.8 mg, 0.813 mmol) and N1-(benzo[d]thiazol-2-yl)ethane-1,2-diamine (212.1 mgs, 0.800 mmol) in dichloromethane (10 mL) was cooled in an ice bath, then treated with triethylamine (0.45 mL, 3.23 mmol) and 1-[3-dimethylaminopropyl]-3-ethyl carbodiimide hydrochloride (163.3 mg, 0.852 mmol). The resulting mixture was stirred overnight at room temperature, then was diluted with dichloromethane, washed with water, dried over sodium sulfate, filtered and concentrated to yield a flaky solid. The solid was purified by flash column chromatography, eluting with 8% methanol in chloroform to yield (S)-tert-butyl 1-(2-(benzo[d]thiazol-2-ylamino)ethylamino)-1-oxo-3-(thiophen-2-yl)propan-2-ylcarbamate as a white amorphous solid.

$^1$HNMR (DMSO-d$_6$) δ 8.32-8.15 (m, 1H), 8.01-7.95 (m, 1H), 7.66 (d, J=7.32 Hz, 1H), 7.39 (d, J=7.86 Hz, 1H), 7.30 (d, J=4.74 Hz, 1H), 7.24-7.19 (m, 1H), 7.04-7.00 (m, 1H), 6.96-6.85 (m, 3H), 4.15-4.03 (m, 1H), 3.41-3.19 (m, 4H), 3.16-2.95 (m, 2H), 1.33 (s, 9H); MS (MH+)=447.

Step D:

(S)-tert-butyl 1-(2-(benzo[d]thiazol-2-ylamino)ethylamino)-1-oxo-3-(thiophen-2-yl)propan-2-ylcarbamate (195.9 mg, 0.439 mmol) was suspended in 1,4-dioxane (4 mL) and treated with 4N HCl in 1,4-dioxane (4 mL, 16.0 mmol). The resulting mixture became homogenous, then a solid separated as the stirring continued for 4 h. The solid was collected by filtration, washed with 1,4-dioxane, then dried in a vacuum oven overnight at room temperature, to yield the title compound as its corresponding hydrochloride salt, as a white solid.

$^1$HNMR (DMSO-d$_6$) δ 9.44-9.14 (br s, 1H), 8.85-8.81 (m, 1H), 8.39 (br s, 3H), 7.77 (d, J=7.67 Hz, 1H), 7.48 (d, J=7.97 Hz, 1H), 7.41-7.39 (m, 1H), 7.35-7.30 (m, 1H), 7.16-7.13 (m, 1H), 6.98-6.95 (m, 2H), 3.96-3.94 (m, 1H), 3.55-3.21 (m, 6H).

Compound #42 MS (M+H) 289, was similarly prepared according to the process described in Example 3 above, by selecting and substituting a suitably substituted reagent for the Boc-(β)-(2-thienyl)-L-alanine in STEP C above.

Example 4

Compound #44

(S)-2-amino-N-(2-(benzo[d]oxazol-2-ylamino)ethyl)pent-4-ynamide hydrochloride

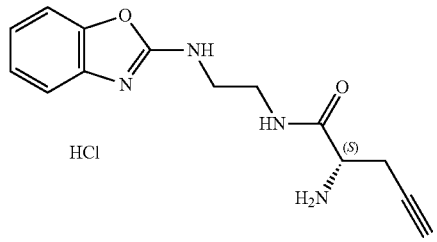

Step A:

A mixture of 2-chlorobenzoxazole (0.6 mL, 5.16 mmol) and N-(2-aminoethyl) carbamic acid tert-butyl ester (2.4328 g, 15.18 mmol)) was stirred in a preheated oil bath at 125° C. for 5 h, then held at room temperature overnight. The solidified mixture was dissolved in chloroform (125 mL), washed with aqueous sodium bicarbonate (2×150 mL), then brine (1×150). The organic layer was dried over sodium sulfate, then filtered and concentrated in vacuo. The resulting residue was purified by flash column chromatography, eluting with 60% ethyl acetate in heptane to yield tert-butyl 2-(benzo[d]oxazol-2-ylamino)ethylcarbamate as a beige powder.

$^1$HNMR (DMSO-d$_6$) δ 7.94-7.90 (m, 1H), 7.32 (d, J=7.83 Hz, 1H), 7.23 (d, J=7.60 Hz, 1H), 7.13-7.07 (m, 1H), 6.99-6.92 (m, 2H), 3.34-3.29 (m, 2H), 3.18-3.12 (m, 2H), 1.37 (s, 9H). MS (MH+)=278.

Step B:

tert-Butyl 2-(benzo[d]oxazol-2-ylamino)ethylcarbamate (515.7 mg, 1.86 mmol) was dissolved in warm p-dioxane (6 mL) and was treated with 4N HCl in 1,4-dioxane (6 mL, 24.0 mmol). The resulting mixture was stirred for 3 h as a solid separated from the acidic solution. Then, additional 4N HCl (2 mL, 8.0 mmol) was added and the resulting mixture stirred for 1 h, then stored in the freezer overnight. The resulting solid was collected by filtration, washed with 1,4-dioxane, then dried in vacuum oven overnight at room temperature to yield the corresponding hydrochloride salt of N$^1$-(benzo[d]oxazol-2-yl)ethane-1,2-diamine as a white powder.

$^1$HNMR (DMSO-d$_6$) δ 8.70 (br s, 1H), 8.16 (s, 3H), 7.43 (d, J=7.85 Hz, 1H), 7.31 (d, J=7.81 Hz, 1H), 7.21-7.16 (m, 1H), 7.10-7.04 (m, 1H), 3.61-3.57 (m, 2H) 3.17-3.06 (m, 2H); MS (MH+)=178.

Step C:

A cold mixture of Boc-L-propargyl-glycine (128.2 mg, 0.602 mmol), N-hydroxybenzotriazole hydrate (84.5 mg, 0.625 mmol) and the hydrochloride salt of N$^1$-(benzo[d]oxazol-2-yl)ethane-1,2-diamine (152.3 mg, 0.609 mmol) in dichloromethane (6 mL) was cooled in an ice bath, then treated with triethylamine (0.34 mL, 2.44 mmol) and 1-[3-dimethylaminopropyl]-3-ethyl carbodiimide hydrochloride (119.6 mg, 0.624 mmol). The resulting mixture was stirred for 40 h at room temperature, then diluted with dichloromethane, washed with water, dried over sodium sulfate, filtered and concentrated to yield a residue The residue was purified by flash column chromatography, eluting with 8% methanol in chloroform to yield (S)-tert-butyl 1-(2-(benzo[d]oxazol-2-ylamino)ethylamino)-1-oxopent-4-yn-2-ylcarbamate as a solid.

$^1$HNMR (DMSO-d$_6$) δ 8.32-8.15 (m, 1H), 7.88 (br s, 1H), 7.32 (d, J=7.83 Hz, 1H), 7.24 (d, J=7.63 Hz, 1H), 7.13-7.08 (m, 1H), 6.99-6.92 (m, 2H), 4.08-4.01 (m, 1H), 3.46-3.33 (m, 4H), 2.81 (s, 1H), 2.58-2.35 (m, 2H), 1.37 (s, 9H). MS (MH+)= 373.

Step D:

(S)-tert-Butyl 1-(2-(benzo[d]oxazol-2-ylamino)ethylamino)-1-oxopent-4-yn-2-ylcarbamate (99.5 mg, 0.267 mmol) was dissolved in 1,4-dioxane (3.5 mL) and treated with 4N HCl in 1,4-dioxane (3.5 mL). The resulting mixture was stirred for 2.5 h and a solid separated from the solution. HCl in 1,4-dioxane (1 mL) was added and the resulting mixture was stirred for 3 h. The solid product was collected by filtration, washed with 1,4-dioxane, then dried in vacuum oven for 1 day at room temperature to yield the title compound as its corresponding hydrochloride salt, as a white solid.

$^1$HNMR (DMSO-d$_6$) δ 9.75-9.40 (br s, 1H), 9.30-9.05 (br s, 1H), 8.91-8.72 (br s, 1H), 8.49 (br s, 3H), 7.45 (d, J=7.94 Hz, 1H), 7.32 (d, J=7.66 Hz, 1H), 7.23-7.19 (m, 1H), 7.11-7.08 (m, 1H), 3.88-3.77 (m, 1H), 3.55-3.21 (m, 4H), 2.76-2.67 (m, 2H), 2.60 (s, 1H).

The following compounds were similarly prepared according to the process described in Example 4 above, by selecting and substituting suitably substituted reagents for the Boc-(β)-(2-thienyl)-L-alanine in STEP C above.

| Compound #45 | MS (M + H) 263 |
| Compound #47 | MS (M + H) 331 |

Example 5

Compound #48

(S)-2-(2-(2-amino-N-methyl-3-(thiophen-2-yl)propanamido)ethylamino)-N-(3,4-di methoxyphenyl)benzo[d]thiazole-6-carboxamide

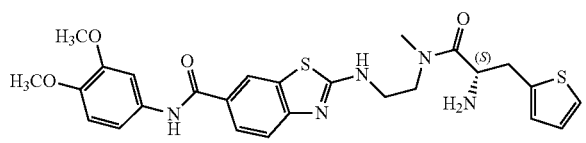

Step A:

2-Bromo-6-benzothiazolecarboxylic acid (496.0 mg, 192 mmol) was suspended in dichloromethane (15 mL), cooled in ice bath, then treated with 2M oxalyl chloride in dichloromethane (2 mL, 4 mmol) and 1 drop of dimethylformamide. The resulting homogenous mixture was stirred for 3 h, then concentrated to a solid. The solid was dissolved in dichloromethane (20 mL), the resulting solution was cooled in an ice bath, then treated with diisopropylethylamine (0.45 mL, 2.58 mmol) and 4-aminoveratole (323.9 mg, 2.11 mmol). The resulting mixture was stirred overnight at room temperature, then diluted with dichloromethane, washed with water, washed with brine, dried over sodium sulfate, filtered and concentrated to yield 2-bromo-N-(3,4-dimethoxyphenyl) benzo[d]thiazole-6-carboxamide as a brown solid.

$^1$HNMR (DMSO-$d_6$) δ 10.3 (s, 1H), 8.69 (s, 1H), 8.10 (s, 2H), 7.47 (d, J=2.23 Hz, 1H), 7.37-7.33 (m, 1H), 6.94 (d, J=8.73 Hz, 1H), 3.76 (s, 3H), 3.75 (s, 3H). MS MH+=393.

Step B:

A mixture of 2-bromo-N-(3,4-dimethoxyphenyl)benzo[d]thiazole-6-carboxamide (392.4 mg, 0.998 mmol), N-(2-aminoethyl)-N-methyl carbamic acid tert-butyl ester (193.4 mg, 1.11 mmol) and N—N-diisopropylethylamine (148.6 mg, 1.15 mmol) in 1-methyl-2-pyrrolidinone (3 mL) was stirred in a preheated oil bath at 120° C. for 4 h, then allowed to cool to room temperature, poured into water and extracted into ethyl acetate. The organic layer was washed with water, dried (sodium sulfate), filtered and concentrated in vacuo. The resulting residue was purified by gradient flash column chromatography, eluting with 70% to 80% ethyl acetate in heptane to yield tert-butyl 2-(6-(3,4-dimethoxyphenylcarbamoyl)benzo[d]thiazol-2-ylamino)ethyl(methyl)carbamate as a beige powder.

$^1$HNMR (DMSO-$d_6$) δ 9.99 (s, 1H), 8.44-8.28 (m, 1H), 8.27 (s, 1H), 7.85 (d, J=8.48 Hz, 1H), 7.61-7.44 (m, 2H), 7.36-7.32 (m, 1H), 6.92 (d, J=8.79 Hz, 1H), 3.75 (s, 3H), 3.74 (s, 3H), 3.61-3.50 (m, 4H), 2.85-2.81 (m, 3H), 1.36-1.26 (m, 9H). MS MH+=487.

Step C:

tert-Butyl 2-(6-(3,4-dimethoxyphenylcarbamoyl)benzo[d]thiazol-2-ylamino)ethyl(methyl)carbamate (327.1 mg, 0.672 mmol) was dissolved in 1,4-dioxane (4 mL) and then treated with 4N HCl in 1,4-dioxane (4 mL, 16.0 mmol). The resulting mixture was stirred for 2 h and a solid separated from the solution. The solid was collected by filtration, washed with 1,4-dioxane, then dried in vacuum oven for 2 d at room temperature to yield the hydrochloride salt of N-(3,4-dimethoxyphenyl)-2-(2-(methylamino)ethylamino)benzo[d]thiazole-6-carboxamide as a yellow solid.

$^1$HNMR (methanol $d_4$) δ 8.36 (d, J=1.53 Hz, 1H), 8.05-8.02 (m, 1H), 7.66 (d, J=8.5 Hz, 1H), 7.42 (d, J=2.3 Hz, 1H), 7.22-7.19 (m, 1H), 6.94 (d, J=8.7 Hz, 1H), 3.96-3.92 (m, 2H), 3.85 (s, 3H), 3.83 (s, 3H), 3.45-3.39 (m, 2H), 2.80 (s, 3H). MS MH+=387.

Step D:

N-(3,4-dimethoxyphenyl)-2-(2-(methylamino)ethylamino)benzo[d]thiazole-6-carboxamide (278.3 mgs, 0.606 mmol), N-hydroxybenzotriazole hydrate (116.6 mg, 0.761 mmol) and Boc-(β)-(2-thienyl)-L-alanine (206.5 mgs, 0.761 mmol) in N—N-dimethylformamide (2 mL) was cooled in an ice bath, then treated with triethylamine (245.2 mL, 2.42 mmol) and 1-[3-dimethylaminopropyl]-3-ethyl carbodiimide hydrochloride (145.9 mg, 0.761 mmol). The resulting mixture was stirred overnight at room temperature. After 18 h, water was added and a solid separated, which solid was collected by filtration. The solid was then washed with additional water and dried under house vacuum. The resulting solid was purified by flash column chromatography, eluting with 4% methanol in chloroform to yield (S)-tert-butyl 1-((2-(6-(3,4-dimethoxyphenylcarbamoyl)benzo[d]thiazol-2-ylamino)ethyl)(methyl)amino)-1-oxo-3-(thiophen-2-yl)propan-2-ylcarbamate as a solid.

$^1$HNMR (DMSO-$d_6$) δ 9.99 (s, 1H), 8.69 (s, 1H), 8.41-8.32 (m, 1H), 8.28 (m, 1H), 7.95-7.85 (m, 2H), 7.61-7.44 (m, 1H), 7.36-7.32 (m, 1H), 6.98-6.95 (m, 3H), 4.65-4.45 (m, 1H), 4.00 (br s, 1H) 3.75 (s, 3H), 3.74 (s, 3H), 3.43 (m, 2H), 3.32 (m, 2H), 3.16-2.95 (m, 2H), 2.90 (s, 3H), 1.40 (s, 9H). MS MH+=640.

Step E:

(S)-tert-Butyl 1-(2-(6-(3,4-dimethoxyphenylcarbamoyl)benzo[d]thiazol-2-ylamino)ethyl)(methyl)amino)-1-oxo-3-(thiophen-2-yl)propan-2-ylcarbamate (286.6 mg, 0.448 mmol) was dissolved in 1,4-dioxane (3 mL) and then treated with 4N HCl in 1,4-dioxane (3 mL, 12.0 mmol). The resulting mixture was stirred for 2.5 h and a yellow solid separated from the solution. The solid was collected by filtration, then washed with 1,4-dioxane (3×10 mL). The resulting hydrochloride salt was converted to its corresponding free base by partitioning between chloroform and aqueous sodium bicarbonate, then purified by preparative thin-layer chromatography, eluting with 90/10/1 chloroform:methanol:concentrated ammonium hydroxide. The free base was dissolved in chloroform (3 mL) and treated with 1N hydrogen chloride in diethyl ether (0.8 mL). The separated solid was covered with diethyl ether, collected by filtration and dried in vacuum oven to yield the title compound as an off-white solid.

$^1$HNMR (DMSO-$d_6$) δ 9.99 (s, 1H), 9.00 (br s, 3H), 8.69 (s, 1H), 8.28 (m, 1H), 7.85 (m, 2H), 7.61-7.44 (m, 1H), 7.36-7.32 (m, 1H), 6.98-6.95 (m, 3H), 4.65-4.45 (m, 3H), 3.75 (s, 3H), 3.74 (s, 3H), 3.43 (m, 2H), 3.32 (m, 2H), 3.26-3.16 (m, 2H), 2.90 (s, 3H).

Example 6

Compound #2

(S)-2-amino-1-(4-(benzo[d]oxazol-2-yl)piperazin-1-yl)-3-(thiophen-2-yl)propan-1-one hydrochloride

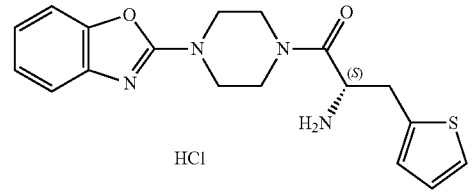

Step A:

2-Piperidino-1,3-benzoxazole (203.6 mgs, 1.00 mmol), N-hydroxybenzotriazole hydrate (138.2 mg, 1.02 mmol) and Boc-β-(2-thienyl)-L-alanine (272.6 mgs, 1.00 mmol) in dichloromethane (10 mL) was cooled in an ice bath, then treated with triethylamine (0.30 mL, 2.15 mmol) and 1-[3-dimethylaminopropyl]-3-ethyl carbodiimide hydrochloride (199.5 mg, 1.04 mmol). The resulting mixture was stirred overnight at room temperature. After 18 h, the resulting mixture was diluted with chloroform and washed with water. The organic layer was dried over sodium sulfate, filtered and concentrated to a residue. The residue was purified by flash column chromatography, eluting with 3% methanol in chloroform to yield (S)-tert-butyl 1-(4-(benzo[d]oxazol-2-yl)piperazin-1-yl)-1-oxo-3-(thiophen-2-yl)propan-2-ylcarbamate as a colorless glass.

¹HNMR (DMSO-d₆) δ 8.31 (s, 1H), 7.36 (d, J=7.83 Hz, 1H), 7.33-7.29 (m, 2H), 7.19-7.14 (m, 1H), 7.06-7.01 (m, 1H), 6.94-6.92 (m, 2H), 4.66-4.53 (m, 1H), 3.80-3.54 (m, 8H), 3.25-0.00 (m, 2H), 1.36 (s, 9H); MS (MH+)=457.

Step B:

(S)-tert-butyl 1-(4-(benzo[d]oxazol-2-yl)piperazin-1-yl)-1-oxo-3-(thiophen-2-yl)propan-2-ylcarbamate (367.5 mg, 0.805 mmol) was dissolved in 1,4-dioxane (5 mL) and treated with 4N hydrogen chloride in 1,4-dioxane (5 mL, 12.0 mmol). The resulting mixture was stirred at room temperature for 3 h, then additional 4N HCl in 1,4-dioxane (1 mL) was added and the resulting mixture stirred for 18 h. The resulting solid was collected by decantation, washed with 1,4-dioxane, and purified by recrystallization from an isopropanol-diethyl ether mixture to yield the title compound as an off-white solid.

¹HNMR (DMSO-d₆) δ 8.43 (s, 3H), 7.46-7.42 (m, 2H), 7.33-7.30 (m, 1H), 7.20-7.15 (m, 1H), 7.08-7.00 (m, 2), 3.73-3.11 (m, 10H); MS (MH+)=357.

Compound #1 MS (M+H) 373 was similarly prepared according to the process described in Example 6 above, by substituting 2-(piperazin-1-yl)benzo[d]thiazole for 2-piperidino-1,3-benzoxazole in STEP A above.

Example 7

Compound #4

(S)-2-(4-(2-aminobutanoyl)piperazin-1-yl)-N-(3,4-dimethoxyphenyl)benzo[d]thiazole-6-carboxamide hydrochloride

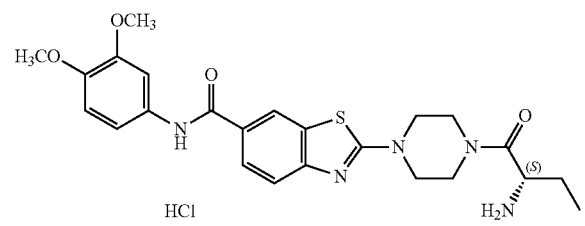

Step A:

2-Bromo-N-(3,4-dimethoxyphenyl)benzo[d]thiazole-6-carboxamide (612.2 mg, 1.56 mmol), N-Boc piperazine (300.8 mg, 1.61 mmol) and diisopropylethylamine (0.3 mL, 1.72 mmol) in N-methyl-2-pyrrolidinone (5.5 mL) was stirred at 120° C. (oil bath) for 4 h, then at room temperature for 18 h. The resulting mixture was diluted with water and the solid separated from the solution. The solid was collected by filtration, dissolved in ethyl acetate, washed with water (2×), then dried, filtered and concentrated. The resulting residue was purified by flash chromatography, eluting with 5% methanol in chloroform to yield tert-butyl 4-(6-(3,4-dimethoxyphenylcarbamoyl)benzo[d]thiazol-2-yl)piperazine-1-carboxylate as a brown glassy solid.

¹HNMR (DMSO-d₆) δ 10.0 (s, 1H), 8.39 (s, 1H), 7.92-7.89 (m, 1H), 7.53 (d, J=8.49 Hz, 1H), 7.47 (d, J=2.1 Hz, 1H), 7.36-7.32 (m, 1H), 6.94 (d, J=8.73 Hz, 1H), 3.75 (s, 3H), 3.74 (s, 3H), 3.64-3.61 (m, 4H), 3.52-3.50 (m, 4H), 1.43 (s, 9H); MS MH+=499.

Step B:

tert-Butyl 4-(6-(3,4-dimethoxyphenylcarbamoyl)benzo[d]thiazol-2-yl)piperazine-1-carboxylate (507.1 mg, 1.15 mmol) was treated with trifluoroacetic acid (24 mL). The resulting homogenous mixture was stirred for 30 min, then diluted with diethyl ether and cooled in ice bath. The resulting solid was collected by filtration and dried in vacuum oven at room temperature to yield N-(3,4-dimethoxyphenyl)-2-(piperazin-1-yl)benzo[d]thiazole-6-carboxamide as a khaki colored amorphous solid.

¹HNMR (DMSO-d₆) δ 10.0 (s, 1H), 9.25 (br s, 2H), 8.45 (s, 1H), 7.93 (d, J=8.43 Hz, 1H), 7.58 (d, J=8.42 Hz, 1H), 7.48 (d, J=2.1 Hz, 1H), 7.36-7.33 (m, 1H), 6.94 (d, J=8.8 Hz, 1H), 3.88-3.84 (m, 4H), 3.75 (s, 3H), 3.74 (s, 3H), 3.28 (m, 4H); MS MH+=399.

Step C:

N-(3,4-dimethoxyphenyl)-2-(piperazin-1-yl)benzo[d]thiazole-6-carboxamide (211.0 mg, 0.412 mmol), N-hydroxybenzotriazole hydrate (70.3 mg, 0.52 mmol) and Boc-L-α-aminobutyric acid (104.8 mg, 0.515 mmol) in N,N'-dimethylformamide (2 mL) was cooled in an ice bath, then treated with triethylamine (0.2 mL, 1.43 mmol) and 1-[3-dimethylaminopropyl]-3-ethyl carbodiimide hydrochloride (104.5 mg, 0.545 mmol). The resulting mixture was stirred overnight at room temperature. After 18 h, water was added and a solid separated, which was collected by filtration. The solid was washed with additional water and dried under house vacuum, then purified by preparative TLC, eluting with 5% methanol in chloroform to yield (S)-tert-butyl 1-(4-(6-(3,4-dimethoxyphenylcarbamoyl)benzo[d]thiazol-2-yl)piperazin-1-yl)-1-oxobutan-2-ylcarbamate as a beige solid.

¹HNMR (CDCl₃) δ 8.24 (d, J=1.65 Hz, 1H), 7.84-7.77 (m, 1H), 7.58 (d, J=8.4 Hz, 1H), 7.48 (d, J=2.3 Hz, 1H), 7.03-6.99 (m 1H), 6.85 (d, J=8.7 Hz, 1H), 5.34 (d, J=8.8 Hz, 1H), 4.63-4.55 (m, 1H), 3.92 (s, 3H), 3.89 (s, 3H), 3.77-3.62 (m, 8H), 1.83-1.66 (m, 1H), 1.60-1.51 (m, 1H), 1.45 (s, 9H), 0.96 (t, J=7.4, 7.4 Hz, 3H); MS MH+=584.

Step D:

The (S)-tert-butyl 1-(4-(6-(3,4-dimethoxyphenylcarbamoyl)benzo[d]thiazol-2-yl)piperazin-1-yl)-1-oxobutan-2-ylcarbamate (142.8 mg, 0.245 mmol) was dissolved in p-dioxane (3 mL), treated with 4N hydrogen chloride in 1,4-dioxane (3 mL, 12.0 mmol) and the resulting mixture was stirred at room temperature for 5.5 h. The resulting heterogenous mixture was concentrated under high vacuum, then covered with diethyl ether and placed under high vacuum for 2 d to yield the title compound as a pale yellow powder.

¹HNMR (CDCl₃) δ 10.0 (s, 1H), 8.50-8.42 (m, 1H), 8.24 (br s, 3H), 7.93 (d, J=8.6 Hz, 1H), 7.58 (d, J=8.4 Hz, 1H), 7.48 (d, J=1.9 Hz, 1H), 7.35 (d, J=8.3 Hz, 1H), 6.93 (d, J=8.9 Hz, 1H), 4.62-4.42 (m, 2H), 3.75 (s, 3H), 3.74 (s, 3H), 3.70-3.59 (m, 8H), 1.82-1.68 (m, 2H), 0.96 (t, J=7.4, 7.4 Hz, 3H); MS MH+=484.

The following compounds were similarly prepared according to the process described in Example 7 above, by selecting and substituting a suitably substituted reagent for the Boc-L-(α)-aminobutyric acid in STEP C.

| Compound #6 | MS (M + H) 536 |
|---|---|
| Compound #12 | MS (M + H) 552 |

Example 8

Compound #3

(S)-2-(4-(2-amino-3-(thiophen-2-yl)propanoyl)piperazin-1-yl)-N-(3,4-dimethoxyphenyl)benzo[d]thiazole-6-carboxamide hydrochloride

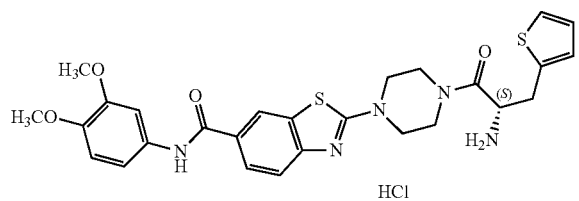

Step A:

N-(3,4-dimethoxyphenyl)-2-(piperazin-1-yl)benzo[d]thiazole-6-carboxamide (1.00 g, 2.51 mmol), Boc-L-2-thienylalanine (0.68 g, 2.551 mmol), diisopropylethylamine (1.75 ml, 10.04 mmol) and HBTU (1.24 g, 3.26 mmol) were dissolved in DMF (71 ml) and stirred overnight. The resulting mixture was diluted with ethyl acetate (154 ml), washed with 1N HCl (3×77 ml), washed with brine (77 ml), dried (MgSO$_4$) and concentrated in vacuo. The resulting residue was chromatographed, eluting with dichloromethane/methanol (97:3) to yield (S)-tert-butyl 1-(4-(6-(3,4-dimethoxyphenylcarbamoyl)benzo[d]thiazol-2-yl)piperazin-1-yl)-1-oxo-3-(thiophen-2-yl)propan-2-ylcarbamate.

$^1$HNMR (CDCl$_3$) δ 8.22 (s, 1H), 7.78-7.76 (m, 2H), 7.57 (d, J=8.4 Hz, 1H), 7.47 (d, J=2.2 Hz, 1H), 7.17 (d, J=5.1 Hz, 1H), 7.01-6.84 (m, 4H), 5.40-5.38 (m, 1H), 4.90-4.85 (m, 1H), 3.92 (s, 3H), 3.89 (s, 3H), 3.80-3.11 (m, 10H), 1.44 (s, 9H).

Step B:

(S)-tert-butyl 1-(4-(6-(3,4-dimethoxyphenylcarbamoyl)benzo[d]thiazol-2-yl)piperazin-1-yl)-1-oxo-3-(thiophen-2-yl)propan-2-ylcarbamate (0.95 g, 1.45 mmol) was dissolved in 1,4-dioxane (2 ml) and treated with 4M HCl in 1,4-dioxane (2 ml). The resulting mixture was stirred at room temperature overnight. The resulting solid was filtered and treated with 4M HCl in 1,4-dioxane (2 ml), again stirring overnight. The solid was filtered, dissolved in dichloromethane and washed with saturated NaHCO$_3$ to yield the title compound as its corresponding free base. The free base was chromatographed eluting with dichloromethane/methanol/ammonium hydroxide to yield the free base as a residue. The free base residue (0.50 g, 0.91 mmol) was dissolved in dichloromethane (2 ml) and treated with 1M HCl in diethyl ether (0.91 ml, 0.91 mmol) and the resulting mixture stirred at room temperature for 2 h. The resulting solid was filtered, washed with diethyl ether (2×) and dried to yield (S)-2-(4-(2-amino-3-(thiophen-2-yl)propanoyl)piperazin-1-yl)-N-(3,4-dimethoxyphenyl)benzo[d]thiazole-6-carboxamide, as its corresponding hydrochloride salt.

$^1$HNMR (CD$_3$OD) δ 8.29 (s, 1H), 7.93-7.90 (m, 1H), 7.56-7.52 (m, 1H), 7.42-7.38 (m, 2H), 7.21-7.11 (m, 1H), 7.09-7.02 (m, 2H), 6.95-6.93 (m, 1H), 4.75-4.72 (m, 1H), 3.85 (s, 3H), 3.93 (s, 3H), 3.80-3.58 (m, 5H), 3.49-3.39 (m, 3H), 3.31-3.22 (m, 2H). ES-MS m/z 552 (MH+);

Calculated for C$_{27}$H$_{29}$N$_5$O$_4$S$_2$HCl 0.03 H$_2$O: C, 54.64; H, 5.220; N, 11.80; Cl, 5.97; H$_2$O, 0.91. Measured: C, 54.93'; H, 5.17; N, 11.67; Cl, 6.11; H$_2$O, 1.18.

Example 9

Compound #19

(S)-2-(4-(2-amino-3-(thiophen-2-yl)propanoyl)piperazin-1-yl)-N-cyclopentylbenzo[d]thiazole-6-carboxamide Step A:

2-Bromo-6-benzothiazolecarboxylic acid (0.500 g, 1.94 mmol) was suspended in dichloromethane/methanol (12 ml, 6:1) and cooled to 0° C. with an ice-water bath. Then, 2M (trimethylsilyl)diazomethane (2.91 ml, 5.81 mmol) was added dropwise over 5 min. The resulting mixture was warmed to room temperature and stirred at room temperature for 2 hrs. The resulting mixture was concentrated in vacuo to yield methyl 2-bromobenzo[d]thiazole-6-carboxylate.

$^1$HNMR (CDCl$_3$) δ 8.55 (s, 1H), 8.15 (d, J=8.6 Hz, 1H), 8.02 (d, J=8.6 Hz, 1H), 3.07 (s, 3H).

Step B:

Methyl 2-bromobenzo[d]thiazole-6-carboxylate (0.52 g, 1.90 mmol), Boc-piperazine (0.44 g, 2.38 mmol) and potassium carbonate (0.53 g, 3.80 mmol) were suspended in acetonitrile (21 ml) and refluxed overnight. The resulting mixture was then cooled to room temperature, concentrated in vacuo to approximately 2 ml, diluted with water and extracted with ethyl acetate. The organic layer was dried (MgSO$_4$) and concentrated in vacuo to yield a residue which was treated with trifluoroacetic acid/dichloromethane (6 ml, 1:1) for 1.5 hrs. The resulting mixture was concentrated in vacuo, the resulting residue was dissolved in dichloromethane and washed with saturated sodium bicarbonate to yield methyl 2-(piperazin-1-yl)benzo[d]thiazole-6-carboxylate.

$^1$HNMR (CDCl$_3$) δ 8.30 (s, 1H), 7.98 (d, J=8.5 Hz, 1H), 7.52 (d, J=8.5 Hz, 1H), 3.91 (s, 3H), 3.68-3.65 (m, 4H), 3.03-3.00 (m, 4H).

Step C:

Methyl 2-(piperazin-1-yl)benzo[d]thiazole-6-carboxylate (0.35 g, 1.26 mmol), Boc-L-2-thienylalanine (0.34 g, 1.26 mmol), diisopropylethylamine (0.88 ml, 5.06 mmol) and HBTU (0.62 g, 1.64 mmol) were dissolved in DMF (36 ml) and the resulting mixture stirred overnight. The resulting mixture was then diluted with ethyl acetate (78 ml), washed with 1N HCl (3×39 ml), washed with brine (39 ml), dried (MgSO$_4$) and concentrated in vacuo. The resulting residue was chromatographed eluting with dichloromethane/methanol (97:3) to yield (S)-methyl 2-(4-(2-(tert-butoxycarbonylamino)-3-(thiophen-2-yl)propanoyl)piperazin-1-yl)benzo[d]thiazole-6-carboxylate.

¹HNMR (CDCl₃) δ 8.31 (s, 1H), 8.00 (d, J=8.5 Hz, 1H), 7.53 (d, J=8.5 Hz, 1H), 7.15 (d, J=4.4 Hz, 1H), 6.93-6.91 (m, 1H) m 6.88-6.87 (m, 1H), 5.39-5.37 (m, 1H), 4.90-4.84 (m, 1H), 3.92 (s, 3H), 3.89-3.83 (m, 1H), 3.69-3.40 (m, 7H), 3.29-3.10 (m, 2H), 1.44 (s, 9H).

Step D:

(S)-methyl 2-(4-(2-(tert-butoxycarbonylamino)-3-(thiophen-2-yl)propanoyl)piperazin-1-yl)benzo[d]thiazole-6-carboxylate (0.61 g, 1.15 mmol) was dissolved in methanol (6 ml) followed by the addition of 1N NaOH (1.26 ml, 1.26 mmol) and the resulting mixture heated to 50° C. overnight. The resulting mixture was then cooled to room temperature, acidified with 10% citric acid and extracted with ethyl acetate. The organic layer was dried (MgSO₄) and concentrated in vacuo to yield (S)-2-(4-(2-(tert-butoxycarbonylamino)-3-(thiophen-2-yl)propanoyl)piperazin-1-yl)benzo[d]thiazole-6-carboxylic acid.

¹HNMR (DMSO) δ 8.39 (s, 1H), 7.89-7.83 (m, 1H), 7.49 (d, J=8.5 Hz, 1H), 7.34-7.32 (m, 2H), 6.94-6.93 (m, 2H), 4.64-4.61 (m, 1H), 3.67-3.48 (m, 8H), 3.20-3.03 (m, 2H), 1.36 (s, 9H).

Step E:

(S)-2-(4-(2-(tert-Butoxycarbonylamino)-3-(thiophen-2-yl)propanoyl)piperazin-1-yl)benzo[d]thiazole-6-carboxylic acid (0.084 g, 0.155 mmol), cyclopentylamine (0.015 ml, 0.155 mmol), diisopropylethylamine (0.11 ml, 0.62 mmol) and HBTU (0.076 g, 0.20 mmol) were dissolved in DMF (4 ml) and the resulting mixture stirred overnight. The resulting mixture was then diluted with ethyl acetate (9 ml), washed with 1N HCl (3×5 ml), brine (5 ml), dried (MgSO₄) and concentrated in vacuo. The resulting residue was chromatographed eluting with dichloromethane/methanol (97:2) to yield a residue which was dissolved in 1,4-dioxane (1 ml) and treated with 4M HCl in 1,4-dioxane for three days. The resulting solid was filtered, washed with ether (3×) and dried to yield (S)-2-(4-(2-amino-3-(thiophen-2-yl)propanoyl)piperazin-1-yl)-N-cyclopentylbenzo[d]thiazole-6-carboxamide (Compound #26).

¹HNMR (CD₃OD) δ 8.24 (s, 1H), 7.89-7.87 (m, 1H), 7.56 (d, J=8.5 Hz, 1H), 7.39-7.37 (m, 1H), 7.06-7.02 (m, 2H), 4.77-4.73 (m, 1H), 4.35-4.28 (m, 1H), 3.84-3.67 (m, 6H), 3.45-3.35 (m, 4H), 2.06-2.01 (m, 2H), 1.80-1.74 (m, 2H), 1.69-1.55 (m, 4H). ES-MS m/z 484 (MH⁺).

The following compounds were similarly prepared according to the process described in Example 9 above, by selecting and substituting a suitably substituted reagent for the cyclopentylamine in STEP E.

| Compound #20 | MS (M + H) 510 |
| Compound #24 | MS (M + H) 472 |
| Compound #25 | MS (M + H) 488 |
| Compound #27 | MS (M + H) 444 |
| Compound #28 | MS (M + H) 536 |
| Compound #29 | MS (M + H) 458 |
| Compound #30 | MS (M + H) 498 |
| Compound #31 | MS (M + H) 536 |

Example 10

Compound #18

(S)-2-amino-1-(4-(6-(hydroxymethyl)benzo[d]thiazol-2-yl)piperazin-1-yl)-3-(thiophen-2-yl)propan-1-one

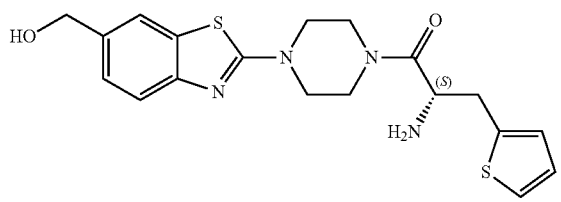

Step A:

Ethyl 2-aminobenzothiazole-6-carboxylate (8.91 g) and CuBr₂ (13.43 g) were combined in acetonitrile (300 mL). To the resulting deep green solution was added tert-butylnitrite (7.14 mL). The resulting mixture was heated to ~65 C for two hours, then concentrated to ~50 mL. The resulting concentrate was diluted with water (250 mL) and extracted with EtOAc (2×250 mL). The resulting yellow solution was concentrated to yield ethyl 2-bromobenzo[d]thiazole-6-carboxylate as a yellow solid.

¹H NMR δ 8.55 (s, 1H), 8.16 (dd, 1H, J=8.6, 1.7 Hz), 8.03 (d, 1H, J=8.3 Hz), 4.43 (q, 2H, J=7.1 Hz), 1.43 (t, 3H, J=7.1 Hz). MS: 286.0 (M+H).

Step B:

The ethyl 2-bromobenzo[d]thiazole-6-carboxylate (11.1 g), BOC-piperazine (9.03 g), potassium carbonate (11.7 g) and acetonitrile (400 mL) were combined and heated to reflux overnight. The resulting mixture was cooled to room temperature, diluted with water and extracted with EtOAc. The organics were concentrated to a yellow solid, which was recrystallized from EtOAc/heptane to yield a ethyl 2-(4-(tert-butoxycarbonyl)piperazin-1-yl)benzo[d]thiazole-6-carboxylate as a white powder, which was collected by filtration.

¹H NMR δ 8.32 (d, 1H, J=1.7 Hz), 8.01 (dd, 1H, J=8.4, 1.8 Hz), 7.54 (d, 1H, J=8.3 Hz), 4.37 (q, 2H, J=7.1 Hz), 3.57-3.69 (m, 8H), 1.49 (s, 9H), 1.40 (t, 3H, J=7.1 Hz). MS: 392.3 (M+H).

Step C:

The ethyl 2-(4-(tert-butoxycarbonyl)piperazin-1-yl)benzo[d]thiazole-6-carboxylate (1.1 g) was dissolved in dry THF (50 mL) and lithium borohydride (67 mg) was added. The resulting mixture was stirred overnight at room temperature, then heated to reflux for 24 hours. Saturated aqueous sodium bicarbonate was added and the resulting mixture was extracted with ethyl acetate. The resulting solution was concentrated to yield tert-butyl 4-(6-(hydroxymethyl)benzo[d]thiazol-2-yl)piperazine-1-carboxylate as a white solid (1.0 g). MS: 350.3 (M+H).

Step D:

The tert-butyl 4-(6-(hydroxymethyl)benzo[d]thiazol-2-yl)piperazine-1-carboxylate (1.0 g) was dissolved in a mixture of TFA (2 mL) and DCM (20 mL) and stirred at room temperature. After four hours, the resulting mixture was concentrated to yield (2-(piperazin-1-yl)benzo[d]thiazol-6-yl)methanol as a yellow oil (0.7 g). MS: 250.3 (M+H).

Step E:

Boc-3-Alanine-(2-thienyl)-OH (0.84 g) and N-ethylmorpholine (1.78 mL) were combined in DMF (25 mL). PyBOP (1.61 g) was added and the resulting mixture stirred at room temperature for 15 min. (2-(piperazin-1-yl)benzo[d]thiazol-6-yl)methanol (0.7 g) was added and the resulting mixture stirred at room temperature overnight, then diluted with ethyl acetate and saturated aqueous sodium bicarbonate. The resulting mixture was extracted with ethyl acetate, concentrated and chromatographed (0 to 5% MeOH in DCM) to yield (S)-tert-butyl 1-(4-(6-(hydroxymethyl)benzo[d]thiazol-2-yl)piperazin-1-yl)-1-oxo-3-(thiophen-2-yl)propan-2-ylcarbamate as a white solid.

$^1$H NMR δ 7.36 (s, 1H), 7.51 (d, 1H, J=8.3 Hz), 7.26-7.30 (m, 1H), 7.15 (d, 1H, J=4.1 Hz), 6.89-6.93 (m, 1H), 6.83-6.87 (m, 1H), 4.80-4.90 (1H, m), 4.71 (2H, s), 2.7-3.9 (m, 10H), 1.44 (s, 9H). MS: 503.3 (M+H).

Step F:

The (S)-tert-butyl 1-(4-(6-(hydroxymethyl)benzo[d]thiazol-2-yl)piperazin-1-yl)-1-oxo-3-(thiophen-2-yl)propan-2-ylcarbamate (83 mg) was dissolved in dry 1,4-dioxane (3 mL) and HCl (4N in 1,4-dioxane, 1 mL) was added. The resulting solution was stirred overnight at room temperature, then concentrated to a white solid. The solid was chromatographed (94.5:5:0.5 dichloromethane:methanol:ammonium hydroxide) to yield the title compound as a colorless oil, which was added to HCl/ether to yield (S)-2-amino-1-(4-(6-(hydroxymethyl)benzo[d]thiazol-2-yl)piperazin-1-yl)-3-(thiophen-2-yl)propan-1-one as a white precipitate, which was collected by filtration.

$^1$H NMR δ 7.63 (s, 1H), 7.51 (d, 1H, J=8.3 Hz), 7.26-7.30 (m, 1H), 7.17 (1H, dd, J=5.1, 1.0 Hz), 6.94 (dd, 1H, J=5.1, 3.4 Hz), 6.85 (d, 1H, J=2.7 Hz), 4.71 (2H, s), 3.0-4.0 (m, 11H). MS: 403.2 (M+H).

Example 11

Compound #21

(S)-2-amino-1-(4-(6-((cyclopentylamino)methyl)benzo[d]thiazol-2-yl)piperazin-1-yl)-3-(thiophen-2-yl)propan-1-one

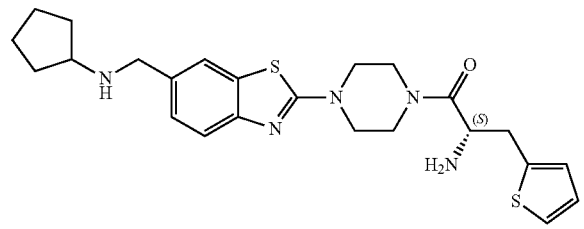

Step A:

(S)-tert-butyl 1-(4-(6-(hydroxymethyl)benzo[d]thiazol-2-yl)piperazin-1-yl)-1-oxo-3-(thiophen-2-yl)propan-2-ylcarbamate (0.859 g) and Dess-Martin reagent (1.09 g) were combined in dry DCM (20 mL) and the resulting mixture stirred at room temperature for 24 hours. The resulting mixture was diluted with saturated aqueous sodium bicarbonate and then extracted with DCM. The combined organic layers were washed with saturated aqueous $Na_2S_2O_3$, concentrated, and chromatographed (0 to 5% MeOH in DCM) to yield (S)-tert-butyl 1-(4-(6-formylbenzo[d]thiazol-2-yl)piperazin-1-yl)-1-oxo-3-(thiophen-2-yl)propan-2-ylcarbamate.

$^1$H NMR δ 9.93 (s, 1H), 8.13 (s, 1H), 7.81 (d, 1H, J=8.3 Hz), 7.60 (d, 1H, J=8.3), 7.10-7.20 (m, 1H), 6.85-6.95 (m, 2H), 5.53-5.70 (m, 1H), 4.84-4.95 (m, 1H), 3.05-3.88 (m, 10H), 1.44 (s, 9H). MS: 501.3 (M+H).

Step B:

(S)-tert-Butyl 1-(4-(6-formylbenzo[d]thiazol-2-yl)piperazin-1-yl)-1-oxo-3-(thiophen-2-yl)propan-2-ylcarbamate (45 mg), cyclopentylamine (12 mg), and sodium triacetoxyborohydride (29 mg) were combined in DCM (1 mL), and the resulting mixture stirred at room temperature overnight, then heated to reflux for 24 hours. The resulting mixture was then cooled to room temperature, quenched with saturated aqueous sodium bicarbonate, extracted with DCM, and chromatographed (0 to 5% MeOH in DCM) to yield (S)-tert-butyl 1-(4-(6-((cyclopentylamino)methyl)benzo[d]thiazol-2-yl)piperazin-1-yl)-1-oxo-3-(thiophen-2-yl)propan-2-ylcarbamate as a colorless oil.

$^1$H NMR δ 8.07 (s, 1H), 7.45-7.65 (m, 2H), 7.15 (s, 1H), 6.82-6.96 (m, 2H), 4.81-4.92 (m, 1H), 2.8-3.9 (m, 13H), 1.26-1.96 (m, 8H), 1.44 (s, 9H). MS: 570.3 (M+H).

Step C:

(S)-tert-Butyl 1-(4-(6-((cyclopentylamino)methyl)benzo[d]thiazol-2-yl)piperazin-1-yl)-1-oxo-3-(thiophen-2-yl)propan-2-ylcarbamate (20 mg) was dissolved in dry 1,4-dioxane (2 ml) and HCl (4N in 1,4-dioxane). 5 mL) was added. The resulting mixture was stirred overnight at room temperature, then concentrated and chromatographed (94.5:5:0.5 dichloromethane:methanol:ammonium hydroxide) to yield a colorless oil, which was added to HCl/diethyl ether. The resulting white precipitate was collected and dried to yield the title compound.

$^1$H NMR δ 7.48-7.66 (m, 2H), 7.15-7.33 (m, 2H), 6.82-6.98 (m, 2H), 3.0-4.0 (m, 14H), 13.-2.0 (m, 8H). MS: 470.2 (M+H).

Example 12

Compound #14

(S)-2-amino-3-(thiophen-2-yl)-1-(4-(6-(4-(trifluoromethyl)phenyl)benzo[d]thiazol-2-yl)piperazin-1-yl)propan-1-one

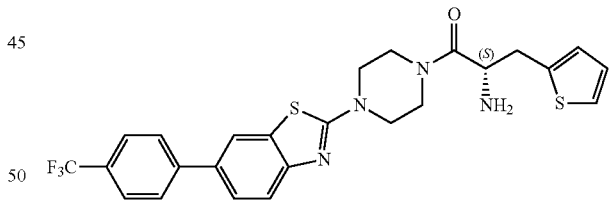

Step A:

2-Chloro-6-bromobenzothiazole (2.29 g), piperazine (1.59 g) and sodium bicarbonate (3.10 g) were combined in isopropanol (75 mL) and the resulting orange solution was heated to reflux overnight, then concentrated to ~15 mL, diluted with water, and extracted with DCM. The extracts were concentrated to yield an orange solid which was chromatographed (0 to 5% MeOH in DCM) to yield 6-bromo-2-(piperazin-1-yl)benzo[d]thiazole as a slightly pink solid. MS: 297.9 (M+H).

Step B:

Boc-3-Alanine-(2-thienyl)-OH (1.32 g) and N-ethylmorpholine (1.54 mL) were dissolved in anhydrous DMF (25 mL) and then PyBOP (2.78 g) was added. The resulting mixture was stirred for 15 min at room temperature, then 6-bromo-2-(piperazin-1-yl)benzo[d]thiazole (1.45 g) was added. The resulting mixture was stirred at room temperature overnight, diluted with saturated aqueous sodium bicarbonate, and extracted with ethyl acetate. The combined organic extracts were washed twice with brine and concentrated to yield a brown oil. The oil was chromatographed (0 to 5% MeOH in DCM) to yield (S)-tert-butyl 1-(4-(6-bromobenzo[d]thiazol-2-yl)piperazin-1-yl)-1-oxo-3-(thiophen-2-yl)propan-2-ylcarbamate as a slightly orange solid. MS: 551.0 (M+H).

Step C:

(S)-tert-Butyl 1-(4-(6-bromobenzo[d]thiazol-2-yl)piperazin-1-yl)-1-oxo-3-(thiophen-2-yl)propan-2-ylcarbamate (80 mg), 4-(trifluoromethyl)phenylboronic acid (33 mg), palladium tetrakistriphenylphosphine (8 mg), and potassium carbonate (54 mg) were combined in 1,4-dioxane (5 mL) and water (1 mL). The resulting mixture was heated to 95° C. overnight, then diluted with brine, extracted with DCM, concentrated, and chromatographed (100% DCM) to yield (S)-tert-butyl 1-oxo-3-(thiophen-2-yl)-1-(4-(6-(4-(trifluoromethyl)phenyl)benzo[d]thiazol-2-yl)piperazin-1-yl)propan-2-ylcarbamate as a colorless oil (96 mg).

$^1$H NMR δ 7.83 (d, 1H, J=1.7 Hz), 7.42-7.74 (m, 6H), 7.16 (d, 1H, J=4.4 Hz), 6.86-6.94 (m, 2H), 5.44-5.52 (1H, m), 4.82-4.93 (m, 1H), 3.0-3.8 (m, 10H), 1.45 (s, 9H); MS: 617.3 (M+H).

Step D:

The (S)-tert-butyl 1-oxo-3-(thiophen-2-yl)-1-(4-(6-(4-(trifluoromethyl)phenyl)benzo[d]thiazol-2-yl)piperazin-1-yl)propan-2-ylcarbamate (96 mg) was dissolved in dry 1,4-dioxane (3 mL) and then HCl (4N in 1,4-dioxane, 1 mL) was added. The resulting mixture was stirred at room temperature overnight, then concentrated and chromatographed (93.5:6: 0.5 DCM:MeOH:NH$_4$OH) to yield a clear oil, which was added to 1N HCl/diethyl ether. The resulting white precipitate was collected by filtration to yield the title compound.

$^1$H NMR δ 7.84 (d, 1H, J=1.7 Hz), 7.53-7.72 (m, 6H), 7.15-7.19 (m, 1H), 6.85-6.95 (m, 2H), 3.0-4.0 (m, 11H); MS: 517.3 (M+H).

Compound #5 MS (M+H) 451, was similarly prepared as described in Example 12 above, by de-protecting the compound prepared in STEP B and reacting (S)-tert-butyl 1-(4-(6-bromobenzo[d]thiazol-2-yl)piperazin-1-yl)-1-oxo-3-(thiophen-2-yl)propan-2-ylcarbamate with HCl.

The following compounds were similarly prepared according to the process described in Example 12 above, by selecting and substituting a suitably substituted reagent for the boronic acid in STEP C.

| Compound #8  | MS (M + H) 463 |
| Compound #9  | MS (M + H) 509 |
| Compound #10 | MS (M + H) 493 |
| Compound #11 | MS (M + H) 485 |
| Compound #13 | MS (M + H) 450 |
| Compound #15 | MS (M + H) 465 |
| Compound #16 | MS (M + H) 467 |
| Compound #17 | MS (M + H) 518 |

Biological Example 1

DPP-1 Inhibition Assay (In Vitro)

Test compounds were assessed for DPP-1 (Cathepsin C) inhibitory activity using a fluorogenic substrate, GR-AMC (Glycine-Arginine-amino-4-methylcoumarin, Bachem, 1-1215). The amount of amino-methylcoumarin released is proportional to the DPP-1 activity, and the reaction is monitored kinetically with a Molecular Devices plate reader using black 96-well plates.

All compounds were tested under room temperature conditions. The assay buffer consisted of 50 mM HEPES, pH 7.0, 100 mM NaCl, 2 mM glutathione (GSH), and 0.002% TWEEN 20. GSH and TWEEN 20 were added to the buffer fresh daily. Just prior to use, an in-house preparation of recombinant human DPP-1 (240 μM stock, MW 49.6 kD) was diluted 600-fold in assay buffer containing fresh 2 mM dithiothreitol (DTT) to activate the enzyme, then diluted into assay buffer (without DTT) 133-fold for a DPP-1 working solution of 3 nM. Test compounds were diluted in DMSO for 20× their final assay concentrations.

Additions to a 96-well black Costar 3915 plates were as follows: 90 μL of 11 μM GR-AMC, 5 μL test compound (followed by mixing), and 5 μL 3 nM DPP1 to start the reaction. Fluorescent reactions were monitored kinetically at 360 nm excitation, 440 nm emission on a Molecular Devices Spectramax XPS reader. The Softmax Pro software of the reader determined the initial velocity of the selected data (the first 3-5 minutes of the reaction), and the best linear regression fit of the initial kinetic data. Final assay conditions were 0.15 nM DPP-1, 10 uM GR-AMC, 50 mM HEPES, pH 7.0, 100 mM NaCl, 2 mM GSH, 0.002% TWEEN 20, 1 μM DTT, 5.0% DMSO. Initial velocity rates were plotted vs. test compound concentration by use of a four-parameter logistics equation (nonlinear regression, sigmoidal dose-response (variable slope), with fixed Hill (1.0) using GraphPad Prism® software for determination of DPP-1 IC$_{50}$. Within-run assay coefficient of variation (CV) was generally <10%; between-run CV<20%.

Representative compounds of the present invention were tested according to the procedure as described above, with results as listed in Table 3, below. Where a compound was tested according to the above procedure multiple times, the average value is listed in Table 3, below.

TABLE 3

| DPP-1 Inhibition | |
|---|---|
| ID No | IC$_{50}$ (μM) |
| 1 | 3.5 |
| 2 | 1.4 |
| 3 | 0.17 |
| 4 | 3.0 |
| 5 | 1.3 |
| 6 | 2.1 |
| 8 | 1.1 |
| 9 | 0.23 |
| 10 | 0.51 |
| 11 | 0.97 |
| 12 | 5.6 |
| 13 | 0.37 |
| 14 | 1.3 |
| 15 | 0.22 |
| 16 | 0.58 |
| 17 | 1.5 |
| 18 | 0.76 |
| 19 | 0.87 |
| 20 | 0.56 |
| 21 | 0.52 |
| 24 | 0.82 |
| 25 | 1.1 |
| 26 | 9.6 |
| 27 | 2.2 |
| 28 | 1.2 |
| 29 | 2.1 |
| 30 | 2.3 |
| 31 | 1.2 |

TABLE 3-continued

DPP-1 Inhibition

| ID No | IC$_{50}$ (μM) |
|---|---|
| 41 | 18.0 |
| 42 | 4.7 |
| 43 | 12.0 |
| 44 | 3.1 |
| 45 | ~8.0 |
| 46 | 0.74 |
| 47 | 0.70 |
| 48 | 0.20 |

Solid, Oral Dosage Formulation

Prophetic Example

As a specific embodiment of an oral composition, 100 mg of the Compound #3, prepared as in Example 8, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A compound of formula (I)

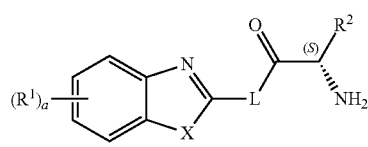

wherein
a is an integer from 0 to 1;
R$^1$ is selected from the group consisting of halogen, C$_{1-4}$alkyl, —CH$_2$—OH, C$_{1-4}$alkoxy, phenyl, 5 to 6 membered heteroaryl, benzo[d][1,3]dioxolyl, —CO$_2$H, —C(O)—NR$^A$R$^B$, —C(O)—NH—(C$_{1-4}$alkyl)-O—(C$_{1-4}$alkyl), —C(O)—NH-phenyl, —C(O)—NH—CH$_2$-phenyl, —C(O)—NH—C$_{3-6}$cycloalkyl and —CH$_2$—NH—C$_{3-6}$cycloalkyl;
wherein R$^A$ and R$^B$ are each independently selected from the group consisting of hydrogen and C$_{1-4}$alkyl;
and wherein the phenyl, whether alone or as part of a substituent group is optionally substituted with one or more substituents independently selected from halogen, hydroxy, C$_{1-4}$alkyl, fluorinated C$_{1-4}$alkyl, C$_{1-4}$alkoxy and fluorinated C$_{1-4}$alkoxy;
X is selected from the group consisting of O and S;
L is selected from the group consisting of —NH—CH$_2$CH$_2$—N(R$^C$)— and

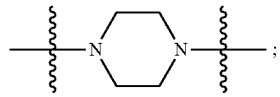

wherein R$^C$ is selected from the group consisting of hydrogen, methyl and ethyl;
R$^2$ is selected from the group consisting of C$_{1-4}$alkyl, C$_{2-4}$alkenyl, C$_{2-4}$alkynyl, —CH$_2$-thienyl and —CH$_2$-furyl;
or a pharmaceutically acceptable salt thereof.

2. A compound as in claim 1, wherein
a is an integer from 0 to 1;
R$^1$ is selected from the group consisting of halogen, C$_{1-2}$alkyl, —CH$_2$—OH, C$_{1-4}$alkoxy, phenyl, 5 to 6 membered heteroaryl, benzo[d][1,3]dioxolyl, —CO$_2$H, —C(O)—NR$^A$R$^B$, —C(O)—NH—(C$_{1-4}$alkyl)-O—(C$_{1-4}$alkyl), —C(O)—NH-phenyl, —C(O)—NH—CH$_2$-phenyl, —C(O)—NH—C$_{3-6}$cycloalkyl and —CH$_2$—NH—C$_{3-6}$cycloalkyl;
wherein R$^A$ and R$^B$ are each independently selected from the group consisting of hydrogen and C$_{1-4}$alkyl;
and wherein the phenyl, whether alone or as part of a substituent group is optionally substituted with one or more substituents independently selected from halogen, hydroxy, C$_{1-2}$alkyl, fluorinated C$_{1-2}$alkyl, C$_{1-4}$alkoxy and fluorinated C$_{1-2}$alkoxy;
X is selected from the group consisting of O and S;
L is selected from the group consisting of —NH—CH$_2$CH$_2$—N(R$^C$)— and

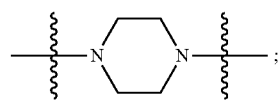

wherein R$^C$ is selected from the group consisting of hydrogen, methyl and ethyl;
R$^2$ is selected from the group consisting of C$_{1-4}$alkyl, C$_{2-4}$alkynyl, —CH$_2$-thienyl and —CH$_2$-furyl;
or a pharmaceutically acceptable salt thereof.

3. A compound as in claim 2, wherein
a is an integer from 0 to 1;
R$^1$ is selected from the group consisting of halogen, —CH$_2$—OH, C$_{1-2}$alkoxy, phenyl, 6 membered heteroaryl, benzo[d][1,3]dioxolyl, —CO$_2$H, —C(O)—NR$^A$R$^B$, —C(O)—NH—(C$_{1-4}$alkyl)-O—(C$_{1-2}$alkyl), —C(O)—NH-phenyl, —C(O)—NH—CH$_2$-phenyl, —C(O)—NH—C$_{5-6}$cycloalkyl and —CH$_2$—NH—C$_{5-6}$cycloalkyl;
wherein R$^A$ and R$^B$ are each independently selected from the group consisting of hydrogen and C$_{1-4}$alkyl;
and wherein the phenyl, whether alone or as part of a substituent group is optionally substituted with one to two substituents independently selected from halogen, hydroxy, C$_{1-2}$alkyl, CF$_3$ and C$_{1-2}$alkoxy;
X is selected from the group consisting of O and S;
L is selected from the group consisting of —NH—CH$_2$CH$_2$—N(R$^C$)— and

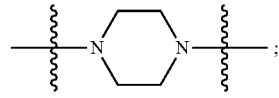

wherein R$^C$ is selected from the group consisting of hydrogen and methyl;
R$^2$ is selected from the group consisting of C$_{1-2}$alkyl, C$_{2-4}$alkynyl, —CH$_2$-thienyl and —CH$_2$-furyl;
or a pharmaceutically acceptable salt thereof.

4. A compound as in claim 3, wherein a is an integer from 0 to 1;

R¹ is selected from the group consisting of 6-(bromo), 6-(carboxy), 6-(hydroxymethyl), 6-(methoxy), 6-(benzo[d][1,3]dioxol-5-yl), 6-(pyrid-3-yl), 6-(4-methylphenyl), 6-(3,4-dimethoxyphenyl), 6-(3,4-difluorophenyl), 6-(4-trifluoromethyl-phenyl), 6-(4-hydroxyphenyl), 6-(2-fluorophenyl), 6-(3,5-dichlorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), 6-(methoxy-n-propyl-amino-carbonyl), 6-(dimethylamino-carbonyl), 6-(4-ethoxyphenyl-amino-carbonyl), 6-(n-propyl-amino-carbonyl), 6-(cyclohexyl-amino-carbonyl), 6-(3-methoxy-benzyl-amino-carbonyl) and 6-(cyclopentyl-amino-methyl);

X is selected from the group consisting of O and S;

L is selected from the group consisting of —NH—CH₂CH₂—NH—, —NH—CH₂CH₂—N(CH₃)— and

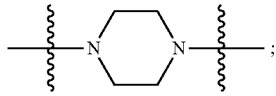

R² is selected from the group consisting of ethyl, n-propyn-2-yl, —CH₂— (thien-2-yl), —CH₂— (thien-3-yl) and —CH₂— (fur-2-yl);

or a pharmaceutically acceptable salt thereof.

5. A compound as in claim 4, wherein a is an integer from 0 to 1;

R¹ is selected from the group consisting of 6-(bromo), 6-(hydroxymethyl), 6-(benzo[d][1,3]dioxol-5-yl), 6-(pyrid-3-yl), 6-(4-methylphenyl), 6-(3,4-dimethoxyphenyl), 6-(3,4-difluorophenyl), 6-(4-trifluoromethyl-phenyl), 6-(4-hydroxyphenyl), 6-(2-fluorophenyl), 6-(3,5-dichlorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), 6-(methoxy-n-propyl-amino-carbonyl), 6-(dimethylamino-carbonyl), 6-(4-ethoxyphenyl-amino-carbonyl), 6-(n-propylamino-carbonyl), 6-(cyclohexyl-amino-carbonyl), 6-(3-methoxy-benzyl-amino-carbonyl) and 6-(cyclopentyl-amino-methyl);

X is selected from the group consisting of O and S;

L is selected from the group consisting of —NH—CH₂CH₂—NH—, —NH—CH₂CH₂—N(CH₃)— and

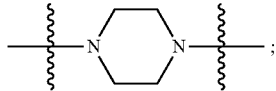

R² is selected from the group consisting of —CH₂—(thien-2-yl) and —CH₂— (fur-2-yl);

or a pharmaceutically acceptable salt thereof.

6. A compound as in claim 5, wherein a is an integer from 0 to 1;

R¹ is selected from the group consisting of 6-(hydroxymethyl), 6-(benzo[d][1,3]dioxol-5-yl), 6-(pyrid-3-yl), 6-(3,4-dimethoxyphenyl), 6-(3,4-difluorophenyl), 6-(4-hydroxyphenyl), 6-(2-fluorophenyl), 6-(3,4-dimethoxyphenyl-amino-carbonyl), 6-(cyclopentyl-amino-carbonyl), 6-(4-fluorophenyl-amino-carbonyl), 6-(n-butyl-amino-carbonyl), and 6-(cyclopentyl-amino-methyl);

X is selected from the group consisting of O and S;

L is selected from the group consisting of —NH—CH₂CH₂—NH—, —NH—CH₂CH₂—N(CH₃)— and

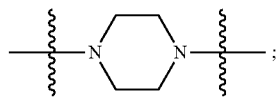 [SMILES: *N1CCN(*)CC1]

R² is —CH₂— (thien-2-yl);

or a pharmaceutically acceptable salt thereof.

7. A compound as in claim 6, wherein a is 1;

R¹ is selected from the group consisting of 6-(benzo[d][1,3]dioxol-5-yl), 6-(pyrid-3-yl), 6-(4-hydroxyphenyl) and 6-(3,4-dimethoxyphenyl-amino-carbonyl);

X is S;

L is selected from the group consisting of —NH—CH₂CH₂—N(CH₃)— and

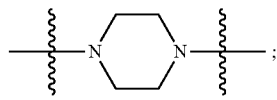

R² is —CH₂— (thien-2-yl);

or a pharmaceutically acceptable salt thereof.

8. A pharmaceutical composition comprising a pharmaceutically acceptable carrier and a compound of claim 1.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

* * * * *